US012730374B2

(12) United States Patent
Shiraishi et al.

(10) Patent No.: US 12,730,374 B2

(45) Date of Patent: Sep. 8, 2026

(54) PHOTOACID GENERATOR, AND PHOTOSENSITIVE COMPOSITION USING SAME

(71) Applicant: SAN-APRO LTD., Kyoto (JP)

(72) Inventors: Atsushi Shiraishi, Kyoto (JP); Futaba Kawakami, Kyoto (JP)

(73) Assignee: SAN-APRO LTD., Kyoto (JP)

(*) Notice: Subject to any disclaimer, the term of this patent is extended or adjusted under 35 U.S.C. 154(b) by 589 days.

(21) Appl. No.: 18/036,994

(22) PCT Filed: Oct. 28, 2021

(86) PCT No.: PCT/JP2021/039794

§ 371 (c)(1),
(2) Date: May 15, 2023

(87) PCT Pub. No.: WO2022/130796

PCT Pub. Date: Jun. 23, 2022

(65) Prior Publication Data

US 2024/0027901 A1 Jan. 25, 2024

(30) Foreign Application Priority Data

Dec. 14, 2020 (JP) ................................ 2020-206433

(51) Int. Cl.
*G03F 7/004* (2006.01)
*C07D 487/22* (2006.01)

(52) U.S. Cl.
CPC ......... *G03F 7/0045* (2013.01); *C07D 487/22* (2013.01)

(58) Field of Classification Search
CPC ............................ G03F 7/0045; G03F 7/0042
See application file for complete search history.

(56) References Cited

U.S. PATENT DOCUMENTS 5,166,197 A * 11/1992 Kenney ................. C09B 47/045 514/183
6,602,645 B1 8/2003 Nakamura et al.
2014/0228561 A1 8/2014 Ema et al.
2020/0048394 A1* 2/2020 Hoevel ..................... C08F 2/48

FOREIGN PATENT DOCUMENTS

| | | | |
|---|---|---|---|
| JP | 2-157760 | A | 6/1990 |
| JP | 5-247110 | A | 9/1993 |
| JP | 9-183960 | A | 7/1997 |
| JP | 11-279212 | A | 10/1999 |
| JP | 2000-352817 | A | 12/2000 |
| JP | 2004-301915 | A | 10/2004 |
| JP | 2007-224229 | A | 9/2007 |
| JP | 2009-19142 | A | 1/2009 |
| JP | 2019-119856 | A | 7/2019 |
| JP | 2019-151770 | A | 9/2019 |
| JP | 2020-64099 | A | 4/2020 |
| WO | 2013/042695 | A1 | 3/2013 |

OTHER PUBLICATIONS

Pappasa et al., "Anthracene-Bound Sulfonium Salts. Highly Efficient Photoinitiators for Cationic Polymerization. A New Synthesis of Sulfonium Salts which Avoids the Use of Silver Salts", Journal of Photopolymer Science and Technology, 2001, vol. 14, No. 5, pp. 703-716, (14 pages).
International Search Report dated Dec. 28, 2021, issued in counterpart International Application No. PCT/JP2021/039794 (3 pages).

* cited by examiner

*Primary Examiner* — Daborah Chacko-Davis
(74) *Attorney, Agent, or Firm* — WHDA, LLP

(57) ABSTRACT

Provided are: a photoacid generator that effectively generates acid even when a substance such as a colorant which attenuates or blocks radiated light is present at a high concentration, the film thickness thereof is large, and a light source is visible light to infrared light, particularly infrared light having low energy; and a highly curable photosensitive composition using the photoacid generator. The present invention is a photoacid generator that is a metal complex having, as a ligand, a ring structure formed by bonding five-membered ring aromatic heterocyclic compounds directly or by n-conjugation, wherein a central metal has one or two axial ligands, and the axial ligand has an onium salt structure.

4 Claims, No Drawings

PHOTOACID GENERATOR, AND PHOTOSENSITIVE COMPOSITION USING SAME

TECHNICAL FIELD

The present invention relates to an acid generating compound which has photosensitivity to light in a visible to infrared region and to a photosensitive composition using the same. More particularly, the present invention relates to a photosensitive composition (e.g. a coating agent, a coating material, a lithographic printing plate or the like) which is cured by radiating light in a visible to infrared region to utilize a generating acid; or to a photoacid generator that is suitably used for production of a product or member (e.g. a material for forming an electronic component, an optical product or an optical component, a layer forming material, an adhesive or the like) which is formed through patterning utilizing a difference between solubility of an exposed portion and solubility of an unexposed portion in a developing solution, by using an acid catalyzed reaction of a generating acid by radiating light in a visible to infrared region.

BACKGROUND ART

A UV curing technique for curing a liquid substance by ultraviolet (UV) irradiation has been expanding to a wide application range including coating agents, coating materials, printing inks and the like, because of its workability (fast curability) and reduced VOC.

In general, a photocurable coating agent comprises a photopolymerization initiator, a radical (cationic) polymerizable monomer, an oligomer or a polymer, and a colorant and additive depending on a use. Colorants are classified broadly into pigments and dyes, and blended for coloring a coating film. A colorant not only blocks light, but also has light absorption property corresponding to the color of the colorant, and thus absorbs a part of radiated light, and therefore when a photocurable coating agent containing a colorant is used, there is a case where light does not reach the deep part of the applied coating film. In this connection, use of a specific photopolymerization initiator has been suggested (see, for example, Patent Document 1).

In addition, for using as a light source a small and inexpensive semiconductor laser that is used for a recording material or the like, sensitivity to a long wavelength, particularly to a near infrared region is required. However, a known photosensitive composition does not have sensitivity to a near infrared region, or does not have sufficiently high sensitivity even if it has sensitivity, and there is a disadvantage that the photosensitive composition does not have sufficient preservability when having high sensitivity.

Thus, a specific initiator has been proposed as an initiator having high sensitivity in a long wavelength region (see, for example, Patent Documents 2 and 3).

However, even photosensitive compositions using specific initiators as described in Patent Documents 1 to 3 have such problems that the curability is not sufficient when a substance such as a colorant which attenuates or blocks irradiated light is present at a high concentration, the film thickness is large, or the light source is in a long wavelength region, and the solubility of the initiator in the composition is low.

Using a sensitizer is well known to increase efficiency of an initiator (see, for example, Patent Documents 4 and 5). An initiator incorporated a complicated structure to the initiator structure directly to adjust an absorption region of the initiator directly is complicated to synthesize and is unfavourable with cost. So, a method of using a sensitizer as a co-initiator is considered easy as the wavelength region becomes longer. On the other hand, a combination use of a sensitizer and an initiator is not easy to determine an effective add amount and a ratio of the both components. Also, there has a problem that a sensitization effect of the combination use is insufficient because of a solubility difference of the both components to a photosensitive composition.

A compound linked by a covalent bond between an initiator and a sensitizer was reported as a means of increasing a sensitization effect (see, Non-Patent Document 1). However, there has a remaining problem that a sensitizer used in a visible to near infrared region has a large molecule and a complicated structure, so, changing the structure is difficult to synthesize as described above, to increase efficiency of an initiator.

PRIOR ART DOCUMENTS

Patent Documents

Patent Document 1: JP-A-2009-19142
Patent Document 2: JP-A-2-157760
Patent Document 3: JP-A-5-247110
Patent Document 4: JP-A-11-279212
Patent Document 5: JP-A-9-183960

Non-Patent Documents

Non-Patent Document 1: S. P. Pappas, J. Photopolym. Sci. Technol., 2001, 14, 703-716.

SUMMARY OF THE INVENTION

Problems to be Solved by the Invention

An object to be achieved by the present invention is to provide a photoacid generator that effectively generates an acid even when a substance such as a colorant which attenuates or blocks radiated light is present at a high concentration, the film thickness thereof is large, and a light source is visible light to infrared light, particularly infrared light having low energy; and a highly curable photosensitive composition using the photoacid generator.

Means for Solving the Problems

The present inventors have extensively conducted studies for solving said problems, and resultantly found a photoacid generator having excellent sensitivity to visible light to infrared light.

That is, the present invention provides a photoacid generator that is a metal complex having, as a ligand, a ring structure formed by bonding five-membered ring aromatic heterocyclic compounds directly or by $\pi$-conjugation, wherein a central metal has one or two axial ligands, and the axial ligand has an onium salt structure.

The present invention also provides a photosensitive composition comprising the above photoacid generator and a cationically polymerizable compound.

The present invention further provides a cured product obtained by curing the above photosensitive composition.

Effects of the Invention

A photoacid generator of the present invention generates a strong acid efficiently by exposing to light in a visible to infrared region with a wavelength of 400 nm to 1500 nm, and can be used in a reaction (an acid catalyzed reaction, a cationic polymerization reaction or the like) by utilizing the strong acid. Even when a composition contains an additive and a colorant having an absorption in an ultraviolet light to visible light region, a cured product can be efficiently produced because transmission of an energy ray is not hindered.

MODE FOR CARRYING OUT THE INVENTION

Hereinafter, embodiments of the present invention are described in detail.

A photoacid generator of the present invention is a metal complex having, as a ligand, a ring structure formed by bonding five-membered ring aromatic heterocyclic compounds directly or by π-conjugation, wherein a central metal has one or two axial ligands, and the axial ligand has an onium salt structure.

A five-membered ring aromatic heterocyclic compound of the present invention is an aromatic compound having cyclic structure with five atoms which contain a carbon atom and one or more heteroatoms (for example, a nitrogen atom, an oxygen atom, a sulfur atom, a phosphorus atom, a silicon atom and the like). Examples of the five-membered ring aromatic heterocyclic compound include furan, thiophene, pyrrole, oxazole, thiazole, imidazole, thiadiazole, triazole and the like, preferably furan, thiophene and pyrrole, more preferably pyrrole from the viewpoint of availability of industrial raw materials.

A compound having a ring structure formed by bonding five-membered ring aromatic heterocyclic compounds directly or by π-conjugation of the present invention (hereinafter abbreviated as a cyclic compound) is a compound group having a ring structure which comprises three to four five-membered ring aromatic heterocyclic compounds, and formed by bonding directly or via one or more carbon atoms and heteroatoms (for example, a nitrogen atom, an oxygen atom, a sulfur atom, a phosphorus atom, a silicon atom and the like) with maintaining π-conjugation. The cyclic compound is a site of absorption. From the viewpoint of availability of industrial raw materials, examples of the cyclic compound include porphyrin, porphyrazine, corrole, phthalocyanine, subporphyrin, subphthalocyanine, chlorin, porphycene and corrphycene, preferably porphyrin and phthalocyanine.

In the present invention, the cyclic compound is used as a ligand of the metal complex (hereinafter abbreviated as a cyclic ligand). The metal complex has one metal element to one molecule of the cyclic compound and the cyclic ligand. Here, an unshared electron pair on the heteroatom of the cyclic ligand is coordinated to a vacant orbit of the metal element.

In the present invention, the metal complex has an axial ligand furthermore. The axial ligand means a ligand coordinated perpendicular to the metal, against the cyclic ligand plane. The axial ligand has an onium salt structure. The cyclic ligand as a site of absorption absorbs light, and the onium salt decomposes to generate an acid.

The photoacid generator of the present invention has a structure represented by general formula (1) or general formula (2), preferably.

[Chemical Formula 1]

(1)

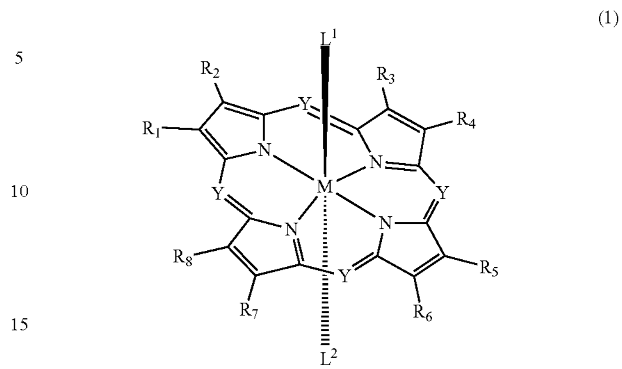

[In formula (1), $R_1$ to $R_8$ are a substituent of the aromatic heterocycle, $R_1$ and $R_2$, $R_3$ and $R_4$, $R_5$ and RG, $R_7$ and $R_8$ may be bonded each other to form a condensed polycyclic aromatic structure; Y represents a nitrogen atom, a carbon atom or may be bonded directly, when Y represents a carbon atom, the carbon atom is substituted with a hydrogen atom or an aromatic hydrocarbon having 6 to 14 carbon atoms; M is selected from the group consisting of Al, Ga, In, Si, Ge, Sn, Fe, Ti, Co and Mn; $L^1$ and $L^2$ are an axial ligand coordinated to the central matal, represented by formula (3), when M is Al, Ga, In, Fe, Co or Mn, the central matal has $L^1$ only as the axial ligand.]

[Chemical Formula 2]

(2)

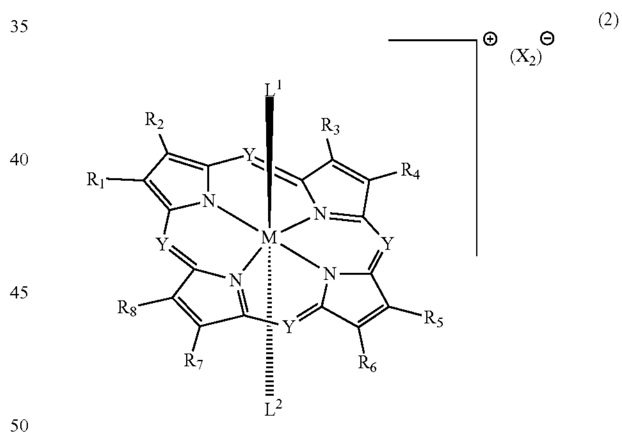

[Formula (2) represents a case when the central matal M is cationic; $R_1$ to $R_8$, Y, $L^1$ and $L^2$ are the same as these of formula (1); M is selected from the group consisting of P, Sb and Bi; $X_2^-$ represents a monovalent counter anion corresponding to the central matal cation.]

[Chemical Formula 3]

(3)

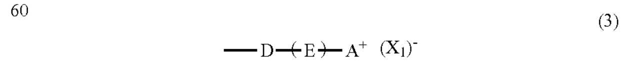

[In formula (3), D represents an oxygen atom or a sulfur atom; E represents an alkylene group having 1 to 8 carbon atoms, an alkenylene group having 2 to 8 carbon atoms, an alkynilene group having 2 to 8 carbon atoms or an arylene group having 6 to 14 carbon atoms, a main chain of E may contain an ether group, a sulfide group, a ketone group, an amide group, an ester group, a thioester group, an urea group, a sulfone group, a silyl group or a phenylene group; $A^+$ represents a monovalent onium cation; $X_1^-$ represents a monovalent counter anion corresponding to the onium cation.]

In formula (1) and formula (2), Y represents a nitrogen atom, a carbon atom or may be bonded directly. Here, being bonded directly means that five-membered ring aromatic heterocyclic compounds are bonded directly and formed a ring structure by n-conjugation. When Y represents a carbon atom, the carbon atom may be substituted with a hydrogen atom or an aryl group having 6 to30 carbon atoms.

In formula (1), M is a central metal of a metal complex having a cyclic ligand of the aromatic heterocycle. M is not restricted, as long as it is a metal having an axial ligand, preferred is a metal selected from the group consisting of Al, Ga, In, Si, Ge, Sn, Fe, Ti, Co and Mn, from the viewpoint of availability of industrial raw materials and the matal complex stability.

In formula (2), M is a central metal of a cationic metal complex having a cyclic ligand of the aromatic heterocycle, preferred is a metal selected from the group consisting of P, Sb and Bi, from the viewpoint of availability of industrial raw materials and the matal complex stability.

In formula (1) and formula (2), $R_1$ to $R_8$ are a substituent of the aromatic heterocycle and are independent of each other. Examples of the substituent include an aryl group having 6 to 30 carbon atoms, a heteroaryl group having 4 to 30 carbon atoms, an alkyl group having 1 to 30 carbon atoms, an alkenyl group having 2 to 30 carbon atoms, an alkynyl group having 2 to 30 carbon atoms, a hydroxyl group, an alkoxy group having 1 to 18 carbon atoms, an aryloxy group having 6 to 10 carbon atoms, an alkylcarbonyl group having 2 to 19 carbon atoms, an arylcarbonyl group having 7 to 11 carbon atoms, an alkoxycarbonyl group having 2 to 19 carbon atoms, an aryloxycarbonyl group having 7 to 11 carbon atoms, an arylthiocarbonyl group having 7 to 11 carbon atoms, an acyloxy group having 2 to 19 carbon atoms, an arylthio group having 6 to 20 carbon atoms, an alkylthio group having 1 to 18 carbon atoms, an alkylsulfinyl group having 1 to 18 carbon atoms, an arylsulfinyl group having 6 to 10 carbon atoms, an alkylsulfonyl group having 1 to 18 carbon atoms, an arylsulfonyl group having 6 to 10 carbon atoms, an alkyleneoxy group, an amino group, a cyano group, a nitro group and a halogen group. $R_1$ and $R_2$, $R_3$ and $R_4$, $R_5$ and $R_6$, $R_7$ and Re may be bonded each other to form a condensed polycyclic aromatic structure.

In the above, examples of the aryl group having 6 to 30 carbon atoms include a monocyclic aryl group such as a phenyl group, a biphenyl group and the like; and a condensed polycyclic aryl group such as naphthyl, antracenyl, phenanthrenyl, pyrenyl, chrysenyl, naphthacenyl, benzantracenyl, anthraquinonyl, fluorenyl, naphtoquinone, anthraquinone and the like.

Examples of the heteroaryl group having 4 to 30 carbon atoms include a cyclic group having one to three heteroatoms such as oxygen, nitrogen and sulfur. These groups may be the same or different from one another. Concrete examples of the group include a monocyclic heteroaryl group such as thienyl, furanyl, pyranyl, pyrrolyl, oxazolyl, thiazolyl, pyridyl, pyrimidinyl, pyrazinyl and the like; and a condensed polycyclic heteroaryl group such as indolyl, benzofuranyl, isobenzofuranyl, benzothienyl, isobenzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, dibenzothienyl, xanthonyl, thioxanthonyl, dibenzofuranyl and the like.

Examples of the alkyl group having 1 to 30 carbon atoms include a linear alkyl group such as methyl, ethyl, propyl, butyl, hexadecyl, octadecyl and the like; a branched alkyl group such as isopropyl, isobutyl, sec-butyl, tert-butyl, isopentyl, neopentyl, tert-pentyl, isohexyl and the like; and a cycloalkyl group such as cyclopropyl, cyclobutyl, cyclopentyl, cyclohexyl and the like.

Examples of the alkenyl group having 2 to 30 carbon atoms include vinyl, allyl, 1-propenyl, iso-propenyl, 1-butenyl, 2-butenyl, 3-butenyl, 1-methyl-1-propenyl and the like.

Examples of the alkynyl group having 2 to 30 carbon atoms include ethynyl, 1-propynyl, 2-propynyl, 1-butynyl, 2-butynyl, 3-butynyl, 1-methyl-1-propynyl, 1-methyl-2-propynyl and the like.

Examples of the alkoxy group having 1 to 18 carbon atoms include methoxy, ethoxy, propoxy, isopropoxy, butoxy, isobutoxy, sec-butoxy, tert-butoxy, dodecyloxy and the like.

Examples of the aryloxy group having 6 to 10 carbon atoms include phenoxy, naphthyloxy and the like.

Examples of the alkylcarbonyl group having 2 to 19 carbon atoms include acetyl, trifluoroacetyl, propionyl, butanoyl, 2-methylpropionyl, heptanoyl, 2-methylbutanoyl, 3-methylbutanoyl, octanoyl and the like.

Examples of the arylcarbonyl group having 7 to 11 carbon atoms include benzoyl, 4-tert-butylbenzoyl, naphthoyl and the like.

Examples of the alkoxycarbonyl group having 2 to 19 carbon atoms include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and the like.

Examples of the aryloxycarbonyl group having 7 to 11 carbon atoms include phenoxycarbonyl, naphthoxycarbonyl and the like.

Examples of the arylthiocarbonyl group having 7 to 11 carbon atoms include phenylthiocarbonyl, naphthoxythiocarbonyl and the like.

Examples of the acyloxy group having 2 to 19 carbon atoms include acetoxy, ethylcarbonyloxy, propylcarbonyloxy, isobutylcarbonyloxy, sec-butylcarbonyloxy, tert-butylcarbonyloxy, octadecylcarbonyloxy and the like.

Examples of the arylthio group having 6 to 20 carbon atoms include phenylthio, biphenylthio, methylphenylthio, chlorophenylthio, bromophenylthio, fluorophenylthio, hydroxyphenylthio, methoxyphenylthio, naphthylthio, 4-[4-(phenylthio)benzoyl]phenylthio, 4-[4-(phenylthio) phenoxy]phenylthio, 4-[4-(phenylthio)phenyl]phenylthio, 4-(phenylthio)phenylthio, 4-benzoylphenylthio, 4-benzoylchlorophenylthio, 4-benzoyl-methylthiophenylthio, 4-(methylthiobenzoyl)phenylthio, 4-(p-tert-butylbenzoyl) phenylthio and the like.

Examples of the alkylthio group having 1 to 18 carbon atoms include methylthio, ethylthio, propylthio, tert-butylthio, neopenthylthio, dodecylthio and the like.

Examples of the alkylsulfinyl group having 1 to 18 carbon atoms include methylsulfinyl, ethylsulfinyl, propylsulfinyl, tert-penthylsulfinyl, octhylsulfinyl and the like.

Examples of the arylsulfinyl group having 6 to 10 carbon atoms include phenylsulfinyl, tolylsulfinyl, naphthylsulfinyl and the like.

Examples of the alkylsulfonyl group having 1 to 18 carbon atoms include methylsulfonyl, ethylsulfonyl, propylsulfonyl, isopropylsulfonyl, butylsulfonyl, octhylsulfonyl and the like.

Examples of the arylsulfonyl group having 6 to 10 carbon atoms include phenylsulfonyl, tolylsulfonyl, naphthylsulfonyl and the like.

Examples of the halogen group include fuluoro, chloro, bromo and iodo.

Among $R_1$ to $R_8$ (a substituent of the aromatic heterocycle), an alkyl group having 1 to 6 carbon atoms, an aryl group having 6 to 14 carbon atoms, a hydroxyl group, an alkoxy group having 1 to 6 carbon atoms, an alkylcarbonyl group having 2 to 6 carbon atoms, an arylcarbonyl group having 7 to 11 carbon atoms, an alkylthio group having 1 to 6 carbon atoms, an arylthio group having 6 to 14 carbon atoms, an aryloxy group having 6 to 10 carbon atoms, chloro and fuluoro are preferable; an alkyl group having 1 to 6 carbon atoms, an aryl group having 6 to 14 carbon atoms, a heteroaryl group having 4 to 14 carbon atoms, an alkoxy group having 1 to 6 carbon atoms, an alkylcarbonyl group having 2 to 6 carbon atoms, a benzoyl group, an aryloxy group having 6 to 10 carbon atoms and fuluoro are more preferable.

In formula (2), $X_2^-$ represents a counter anion corresponding to the cationic central matal M, in formula (3), $X_1^-$ represents a counter anion corresponding to the onium cation. Each of the anions represents a monovalent atomic group that can be an anion, and is an anion corresponding to an acid (HX) which is produced by irradiating the photoacid generator of the present invention with light (such as visible light, ultraviolet ray, electron beam, X-ray or the like). $X_1^-$ and $X_2^-$ are not restricted, as long as it represents a halogen anion or a monovalent polyatomic anion. Examples of the anion include $F^-$, $Cl^-$, $Br^-$, $I^-$, $BY_a^-$, $PY_a^-$, $SbY_a^-$, $(Rf)_bPF_{6-b}^-$, $R^9{}_cBY_{4-c}^-$, $R^9{}_cGaY_{4-c}^-$, $R^{10}SO_3^-$, $(R^{10}SO_2)_3C^-$, and $(R^{10}SO_2)_2N^-$.

P represents a phosphorus atom, B represents a boron atom, Sb represents an antimony atom, F represents a fluorine atom, Ga represents a gallium atom. Y represents a halogen atom (preferably a fluorine atom). S represents a sulfur atom, 0 represents an oxygen atom, C represents a carbon atom, and N represents a nitrogen atom.

Rf represents an alkyl group (preferably an alkyl group having 1 to 8 carbon atoms) whose 80% by mole or more of hydrogen atoms are substituted with fluorine atoms. Examples of the alkyl group to be substituted with fluorine for Rf include straight chain alkyl groups (such as methyl, ethyl, propyl, butyl, pentyl, octyl and the like), branched alkyl groups (such as isopropyl, isobutyl, sec-butyl, tert-butyl and the like), and cycloalkyl groups (such as cyclopropyl, cyclobutyl, cyclopentyl, cyclohexyl and the like). The ratio at which the hydrogen atoms of these alkyl groups are substituted with fluorine atoms in Rf is preferably 80% by mole or more, more preferably 90% by mole or more, in particular, preferably 100% by mole, based on the molar number of the hydrogen atoms in the original alkyl group. When the fluorine atom substitution ratio is in the preferred ranges, the photoacid generator will have higher photosensitivity. In particular, preferred examples of Rf include $CF_3$—, $CF_3CF_2$—, $(CF_3)_2CF$—, $CF_3CF_2CF_2$—, $CF_3CF_2CF_2CF_2$—, $(CF_3)_2CFCF_2$—, $CF_3CF_2$ $(CF_3)$ CF—, and $(CF_3)_3C$—. b "Rf"s are independent of one another and therefore may be the same as or different from one another.

$R^9$ represents a phenyl group whose hydrogen atoms are partially substituted with at least one element or an electron-withdrawing group. For example, such one element includes a halogen atom, examples of which include a fluorine atom, a chlorine atom, a bromine atom and the like. Examples of the electron-withdrawing group include a trifluoromethyl group, a nitro group, a cyano group and the like. Among them, preferred is a phenyl group one of whose hydrogen atoms is substituted with a fluorine atom or a trifluoromethyl group. c "$R^9$"s are independent of one another and therefore may be the same as or different from one another.

$R^{10}$ represents an alkyl group having 1 to 20 carbon atoms, a perfluoroalkyl group having 1 to 20 carbon atoms, or an aryl group having 6 to 20 carbon atoms, wherein the alkyl group and the perfluoroalkyl group may each be any of a straight chain, a branched chain, or a cyclic group, and the aryl group may be substituted or unsubstituted.

a represents an integer of 4 to 6.

b represents an integer of 1 to 5, preferably 2 to 4, more preferably 2 or 3.

c represents an integer of 1 to 4, preferably 4.

Examples of the anion represented by $(Rf)_bPF_{6-b}^-$ include anions represented by $(CF_3CF_2)_2PF_4^-$, $(CF_3CF_2)_3PF_3^-$, $((CF_3)_2CF)_2PF_4^-$, $((CF_3)_2CF)_3PF_3^-$, $(CF_3CF_2CF_2)_2PF_4^-$, $(CF_3CF_2CF_2)_3PF_3^-$, $((CF_3)_2CFCF_2)_2PF_4^-$, $((CF_3)_2CFCF_2)_3PF_3^-$, $(CF_3CF_2CF_2CF_2)_2PF_4^-$, and $(CF_3CF_2CF_2CF_2)_3PF_3^-$. Among them, preferred are anions represented by $(CF_3CF_2)_3PF_3^-$, $(CF_3CF_2CF_2)_3PF_3^-$, $((CF_3)_2CF)_3PF_3^-$, $((CF_3)_2CF)_2PF_4^-$, $((CF_3)_2CFCF_2)_3PF_3^-$, and $((CFA)_2CFCF_2)_2PF_4^-$.

Examples of the anion represented by $R^8{}_cBY_{4-c}^-$ include anions represented by $(C_6F_5)_4B^-$, $((CF_3)_2C_6H_3)_4B^-$, $(CF_3C_6H_4)_4B^-$, $(C_6F_5)_2BF_2^-$, $C_6F_5BF_3^-$, and $(CGH_3F_2)_4B^-$. Among them, preferred are anions represented by $(C_6F_5)_4B^-$ and $((CF_3)_2C_6H_3)_4B^-$.

Examples of the anion represented by $R^9{}_cGaY_{4-c}^-$ include anions represented by $(C_6F_5)_4Ga^-$, $((CF_3)_2C_6H_3)_4Ga^-$, $(CF_3C_6H_4)_4Ga^-$, $(C_6F_5)_2GaF_2^-$, $C_6F_5GaF_3^-$, and $(C_6H_3F_2)_4Ga^-$. Among them, preferred are anions represented by $(C_6F_5)_4Ga^-$ and $((CF_3)_2C_6H_3)_4Ga^-$.

Examples of the anion represented by $R^{10}SO_3^-$ include trifluoromethanesulfonate anion, pentafluoroethanesulfonate anion, heptafluoropropanesulfonate anion, nonafluorobutanesulfonate anion, pentafluorophenylsulfonate anion, p-toluenesuifonate anion, benzenesulfonate anion, camphorsulfonate anion, methanesulfonate anion, ethahesulfonate anion, propanesulfonate anion, butanesulfonate anion and the like. Among them, preferred are trifluoromethanesulfonate anion, nonafluorobutanesulfonate anion, methanesulfonate anion, butanesulfonate anion, camphorsulfonate anion, benzenesulfonate anion, and p-toluenesulfonate anion.

Examples of the anion represented by $(R^{10}SO_2)_3C^-$ include anions represented by $(CF_3SO_2)_3C^-$, $(C_2F_5SO_2)_3C^-$, $(C_3F_7SO_2)_3C^-$, and $(C_4F_9SO_2)_3C$.

Examples of the anion represented by $(R^{10}SO_2)_2N^-$ include anions represented by $(CF_3SO_2)_2N^-$, $(C_2F_5SO_2)_2N^-$, $(C_3F_7SO_2)_2N^-$, and $(C_4F_9SO_2)_2N^-$.

Examples of the monovalent polyatomic anion that may be used include not only anions represented by $BY_a^-$, $PY_a^-$, $SbY_a^-$, $(Rf)_bPF_{6-b}^-$, $R^9{}_cBY_{4-c}^-$, $R^9{}_cGaY_{4-c}^-$, $R^{10}SO_3^-$, $(R^{10}SO_2)_3C$—, or $(R^{10}SO_2)_2N^-$ but also perhalogenate ions (such as $ClO_4^-$, $BrO_4^-$ and the like), halogenated sulfonate ions (such as $FSO_3^-$, $ClSO_3^-$ and the like), sulfate ions (such as $CH_3SO_4^-$, $CF_3SO_4^-$, $HSO_4^-$ and the like), carbonate ions (such as $HCO_3^-$, $CH_3CO_3$ and the like), aluminate ions (such as $AlCl_4^-$, $AlF_4^-$, $(^{t-}C_4F_9O)$ $Al^-$ and the like), hexafluoro bismuthate ion ($BiF_6^-$), carboxylate ions (such as $CH_3COO^-$, $CF_3COO^-$, $C_6H_5COO^-$, $CH_3C_6H_4COO^-$, $C_6F_5COO^-$, $CF_3C_6H_4COO^-$ and the like), arylborate ions (such as B $(C_6H_5)_4^-$, $CH_3CH_2CH_2CH_2B$ $(C_6H_5)_3^-$ and the like), thiocyanate ion ($SCN^-$), and nitrate ion ($NO_3^-$).

Among these anions, preferred are $F^-$, $Cl^-$, $Br^-$, $I^-$, $BF_4^-$, $SbF_6^-$, $PF_6^-$, $(Rf)_bPF_{6-b}^-$, $R^9{}_cBY_{4-c}^-$, $R^9{}_cGaY_{4-c}^-$, $R^{10}SO_3^-$, $(R^{10}SO_2)_3C^-$, and $(R^{10}SO_2)_2N^-$; more preferred are $SbF_6^-$, $PF_6^-$, $(CF_3CF_2)_3PF_3$, $((CF_3)_2CF)_3PF_3$—, $(CF_3CF_2CF_2)_3PF_3$—, $(C_6F_5)_4B^-$, $((CF_3)_2C_6H_3)_4B^-$, $(C_6F_5)_4Ga^-$, $((CF_3)_2C_6H_3)_4Ga^-$, $(^{t-}C_4F_9O)_4Al^-$, trifluoromethanesulfonate anion, nonafluorobutanesulfonate anion, $(CF_3SO_2)_3C^-$ and $(CF_3SO_2)_2N^-$, from the viewpoint of solubility to a photosensitive composition. When two or more anion's exist in the same molecule, these anions may be the same as or different from one another.

$L^1$ and $L^2$ in formula (1) and formula (2) are an axial ligand coordinated to the central matal M, represented by formula (3). The number of the axial ligand varies by the kind of M. when the central metal is Al, Ga, In, Fe, Co or Mn, the central matal has one axial ligand, and when the central metal is other than that, the central matal has two axial ligands from the viewpoint of stability of the metal complex. When the central matal has two axial ligands, the ligands may be the same as or different from one another.

In formula (3), D is bonded directly to the central metal M, and represents an oxygen atom or a sulfur atom.

In formula (3), E is a divalent group bonding D and onium cation $A^+$. E represents an alkylene group having 1 to 8 carbon atoms, an alkenylene group having 2 to 8 carbon atoms, an alkynilene group having 2 to 8 carbon atoms or an arylene group having 6 to 14 carbon atoms, and a main chain of E may contain an ether group, a sulfide group, a ketone group, an amide group, an ester group, a thioester group, an urea group, a sulfone group or a silyl group. Here, the main chain is a main skeleton bonding D and onium cation $A^+$.

Examples of the alkylene group having 1 to 8 carbon atoms include a linear alkylene group such as methylene, ethylene, trimethylene, tetramethylene, hexamethylene, octamethylene and the like; a branched alkylene group such as 1-methylethylene, 1-methylethylidene, 1,1-dimethylethylene, 1,2-dimethylethylene, 1-methylpropylidene and the like; and a cycloalkylene group such as cyclopropylene, cyclobutylene, cyclopentylene, cyclopentylidene, cyclohexylene cyclohexylidene and the like.

Examples of the alkenylene group having 2 to 8 carbon atoms include vinylene, 1-propenylene, 2-propenylene, 1-butenylene, 2-butenylene, 3-butenylene, 1-hexenylene, cyclohexenylene, 1,3-butadienylene, 1,3-hexadienylene, 2,4,6-octatrienylene and the like.

Examples of the alkynilene group having 2 to 8 carbon atoms include ethynylene, 1-propynylene, 2-propynylene, 1-butynylene, 2-butynylene, 3-butynylene, 1,3-butadiynylene, hexane-1-en-3-ynylene and the like.

Examples of the arylene group having 6 to 14 carbon atoms include phenylene, naphtylene, anthracenylene and biphenylene.

Examples of E include the following groups, when the main chain contains an ether group, a sulfide group, a ketone group, an amide group, an ester group, a thioester group, an urea group, a sulfone group or a silyl group.

* represents bonding position.

[Chemical Formula 4]

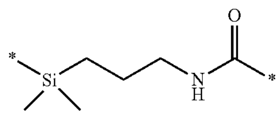

-continued

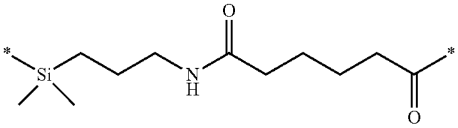

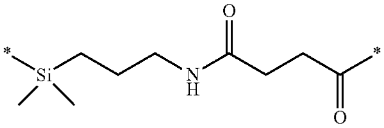

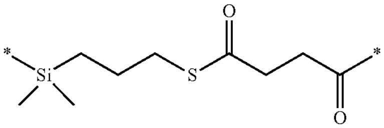

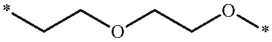

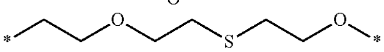

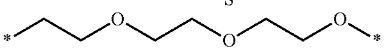

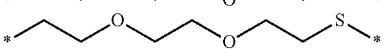

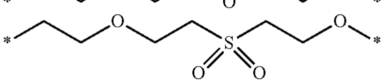

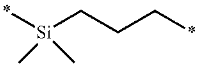

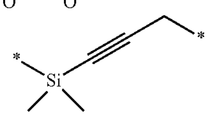

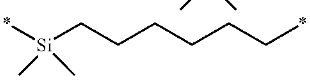

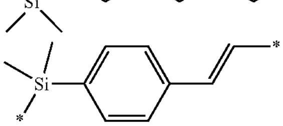

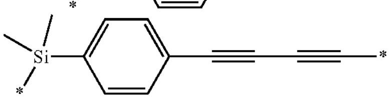

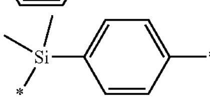

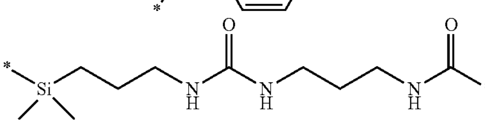

In formula (3), $A^+$ is a monovalent onium cation as an axial ligand, which is bonded a metal via D and E.

The monovalent onium cation means a cation generated by coordinating a proton or a cationic atomic group (e.g. an alkyl group and the like) to a compound containing an element having an unshared electron pair, and examples of the monovalent onium cation include the following cations.

Oxonium cations (trimethyloxonium cation, triethyloxonium, tetramethylenemethyloxonium cation and the like);

Pyririnium cations (4-methylpyririnium cation, 2,6-diphenylpyririnium cation and the like);

Chromenium cations (2,4-dimethylchromenium cation and the like);

Isochromenium cations (1,3-dimethylisochromenium cation and the like);

Ammonium cations [ammonium cations, primary ammonium cations (n-butylammonium cation and the like), secondary ammonium cations (diethylammonium cation and the like), tertiary ammonium cation (triethylammonium cation and the like), quaternary ammonium cations (tetramethylammonium cation, phenyltrimethyl ammonium cation, tetrabutylammonium cation and the like)];

Pyrrolidinium cations (N,N-dimethylpyrrolidinium cation, N,N-diethylpyrrolidinium cation and the like);

Imidazolinium cations (N,N'-dimethylimidazolinium cation, N-ethyl-N'-methylimidazolinium cation and the like);

Amidinium cations (N,N'-dimethyltetrahydropyrimidinium cation, N-benzyl-1,8-diazabicyclo[5.4.0]-7-undecenium cation, N-benzyl-1,5-diazabicyclo[4.3.0]-5-nonenium cation and the like);

Morpholinium cations (N,N'-dimethylmorpholinium cation and the like), piperidium cations (N,N'-diethylpiperidinium cation and the like);

Pyridinium cations (N-methylpyridinium cation, N-methoxypyridinium cation, N-butoxypyridinium cation, N-benzyloxypyridinium cation, N-benzylpyridinium cation and the like);

Imidazolium cations (N,N'-dimethylimidazolium cation, 1-ethyl-3-methylimidazolium cation and the like);

Quinolium cations (N-methylquinolium cation, N-benzyl quinolium cation and the like);

Isoquinolium cations (N-methylisoquinolium and the like);

Thiazonium cations (benzylbenzothiazonium cation and the like);

Acridium cations (benzylacridium cation, phenacylacridium and the like);

Diazonium cations (phenyldiazonium cation, 2,4,6-triethoxyphenyldiazonium cation, 2,4,6-trihexyloxyphenyldiazonium cation and 4-anilinophenyldiazonium cation and the like);

Guanidinium cations (hexamethylguanidinium cation, 2-benzyl-2-tert-butyl-1,1,3,3-tetramethylguanidinium cation and the like);

Phosphonium cations (tertiary phosphonium cations (triphenylphosphonium cation, tri-tert-butylphosphonium cation and the like) and quaternary phosphonium cations (tetraphenylphosphonium cation, tetra-p-tolylphosphonium cation, triphenylbenzylphosphonium cation, triphenylbutyl cation, tetraethylphosphonium cation, tetrabutylphosphonium cation and the like) and the like];

Sulfonium*cations (triphenylsulfonium cation, 4-(phenylthio)phenyldiphenylsulfonium cation, bis[4-(diphenylsulfonio)phenyl]sulfide, 4-hydroxyphenylmethylbenzylsulfonium cation and the like); Sulfoxonium cations (triphenylsulfoxonium and the like);

Thianthrenium cations [5-(4-methoxyphenyl)thianthrenium, 5-phenylthianthrenium, 5-tolylthianthrenium cation and the like];

Thiophenium cations (2-naphthyl tetrahydrothiophenium and the like); and

Iodonium cations [diphenyliodonium cation, di-p-tolyliodonium cation, 4-isopropylphenyl(p-tolyl)iodonium cation and the like].

Among the above described onium cations, sulfonium cations, iodonium cations and diazonium cations are preferable from the viewpoint of photo response.

Specific examples of the preferred axial ligands $L^1$ and $L^2$ represented by formula (3) which contains the sulfonium salt include the following.

[Chemical Formula 5]

(LS-1)

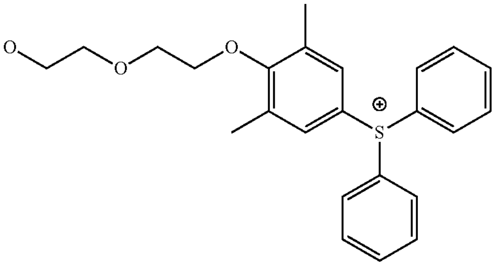

(LS-2)

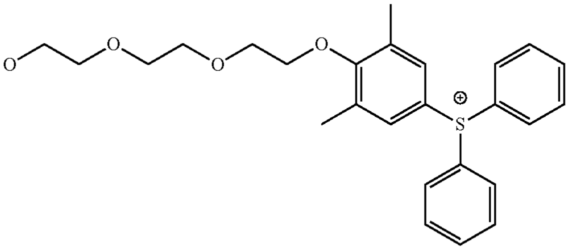

(LS-3)

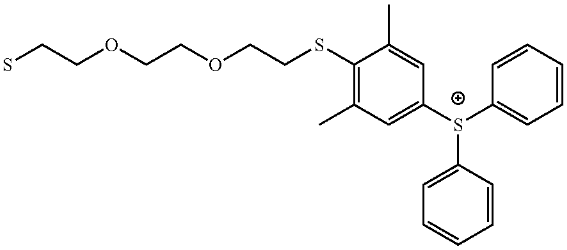

(LS-4)

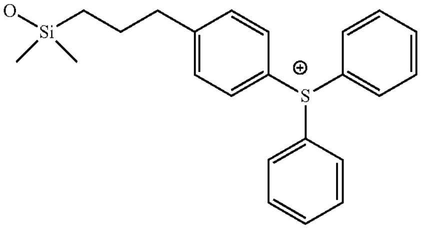

(LS-5)

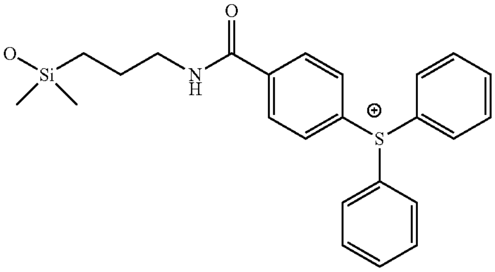

-continued
(LS-6)
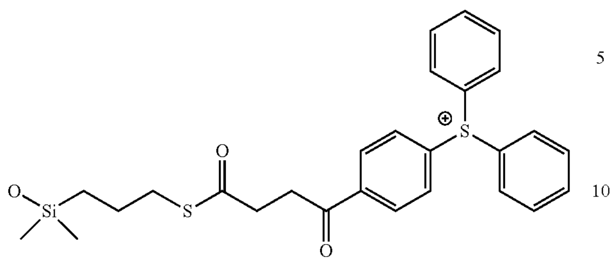
Specific examples of the preferred axial ligands $L^1$ and $L^2$ represented by formula (3) which contains the iodoonium salt include the following.
[Chemical Formula 6]
(LI-1)
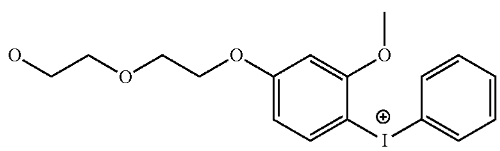
(LI-2)
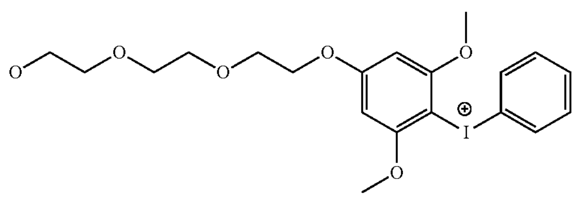
(LI-3)
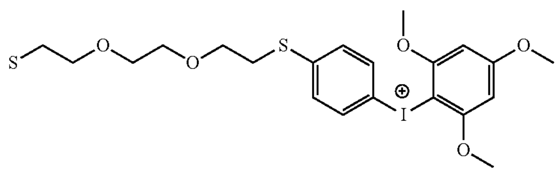
(LI-4)
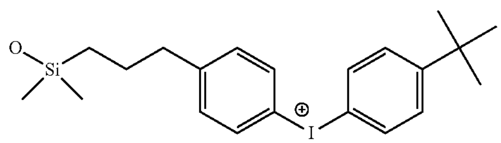
(LI-5)
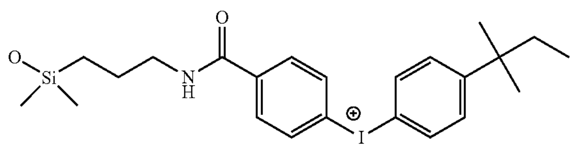
(LI-6)
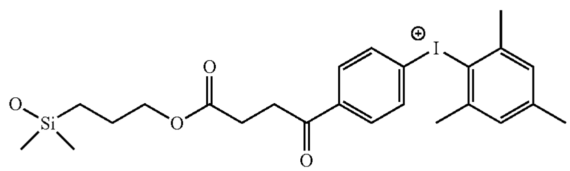
(LI-7)
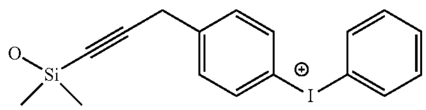
(LI-8)
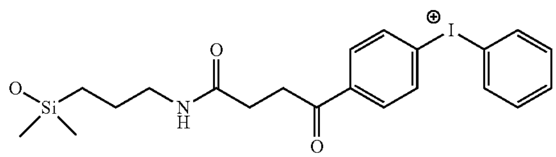
(LI-9)
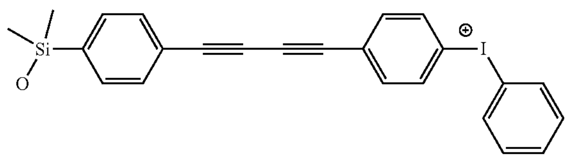
(LI-10)
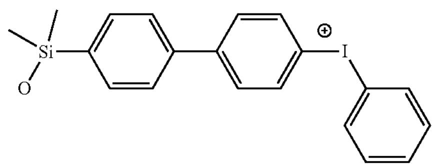

-continued (LI-12)

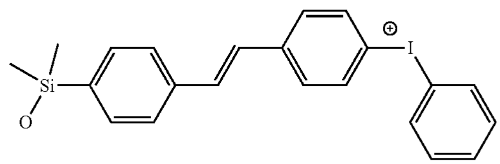

Specific examples of the preferred axial ligands $L^1$ and $L^2$ represented by formula (3) which contains the diazonium salt include the following.

[Chemical Formula 7]

(LN-1)

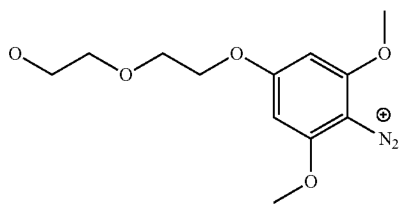

(LN-2)

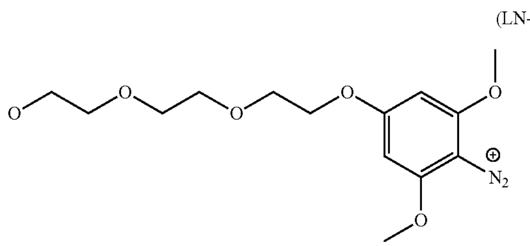

(LN-3)

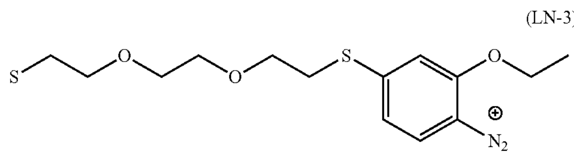

(LN-4)

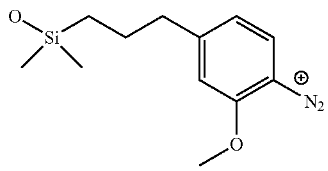

(LN-5)

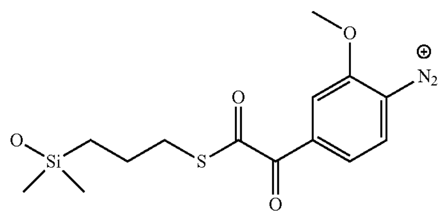

(LN-6)

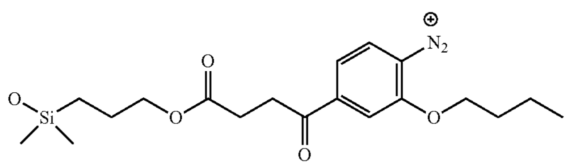

-continued (LN-7)

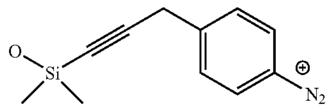

(LN-8)

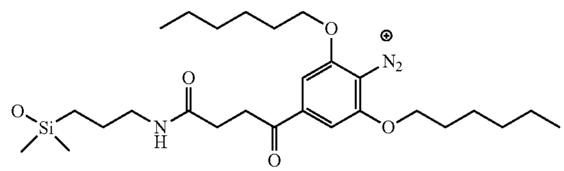

(LN-9)

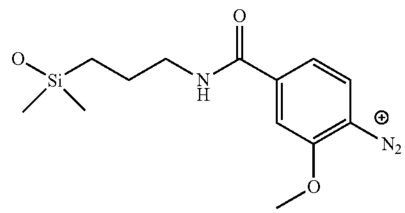

(LN-10)

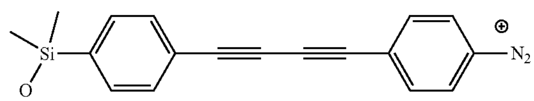

(LN-11)

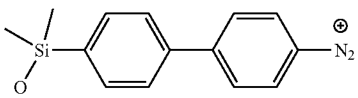

(LN-12)

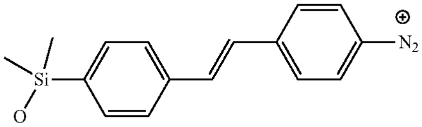

The photoacid generator (Aimed product) represented by the general formula (1) in the present invention can be produced by a known method. A metal complex precursor (a) having an aromatic heterocyclic compound with an aimed site of absorption as a cyclic ligand, and an axial ligand precursor (b) which has an aimed anion and contains an onium structure are synthesized respectively, andthen an aimed compound can be obtained by joining these precursors. An example thereof is shown by the following chemical reaction formulas. (Here, porphyrin is used as an aromatic heterocyclic compound.) By the way, a metal complex precursor (a) can be produced by various known methods. The synthesis method of porphyrins and phthalocyanines is described in, for example, KARL M. KADIS H KEVIN M. SMITH ROGER GUILARD, THE PORPHYRIN HANDBOOK VOL. 1 to 10,ACADEMIC PRESS (2000) and VOL. 11 to 20, (2003).

[Chemical Formula 8]

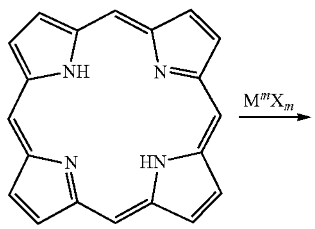

Aromatic heterocyclic compound (CH)

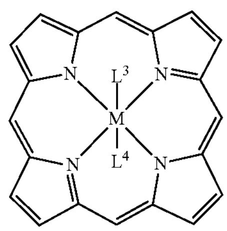

Metal complex precursor (a)

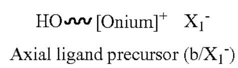

Axial ligand precursor (b/$X_1^-$)

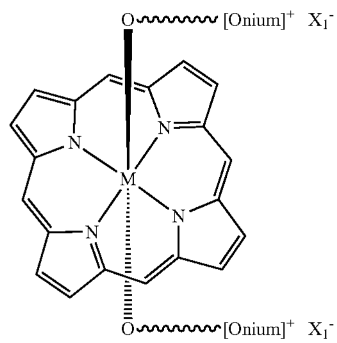

Aimed product

[In formula, M is the same as a central metal M, and m represents valence. X represents a halogen atom, and the number of halogen atom is the same as valence of M. $L^3$ and $L^4$ represent a halogen atom or a hydroxyl group. [Onium] is the same as A in formula (3), and $X_1$ is the same as $X_1$ in formula (3).]

When the photoacid generator (Aimed product) represented by the general formula (2) in the present invention is a cationic metal complex, an aimed compound can be obtained by joining a cationic metal complex precursor (a') and an axial ligand precursor (b) which has an aimed anion and contains an onium structure. At that time, an aimed compound can be obtained by exchanging anions in the presence of equivalent weight or more of an alkaline metal salt or an alkaline earth metal salt of $X_2$ anion, being a raw material, to introduce a counter anion $X_2$ of a central metal cation.

[Chemical Formula 9]

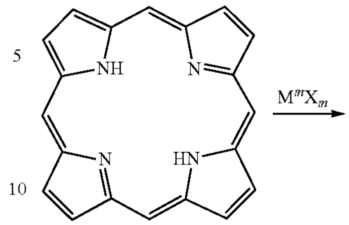

Aromatic heterocyclic Compound (CH)

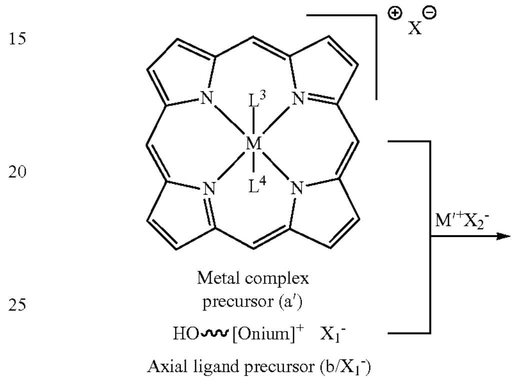

Metal complex precursor (a')

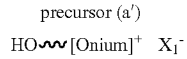

Axial ligand precursor (b/$X_1^-$)

$M'^{+}X_2^{-}$

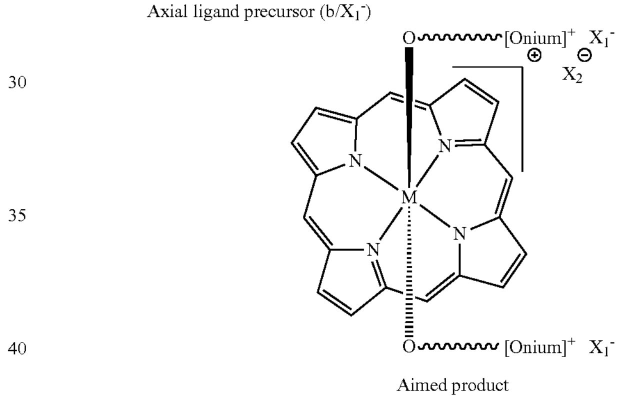

Aimed product

[In formula, M is the same as a central metal M, and m represents valence. X represents a halogen atom, and the number of halogen atom is the same as valence of M. $L^3$ and $L^4$ represent a halogen atom or a hydroxyl group. [Onium] is the same as A in formula (3), $X_1$ is the same as $X_1$ in formula (3), M' represents an alkaline metal or an alkaline earth metal, and $X_2$ is the same as $X_2$ in formula (2).]

The onium cation structure used for an axial ligand precursor (b) in the present invention can be produced by a double decomposition method. In the double decomposition method which is described in, for example, New Experimental Chemistry Vol. 14-I (Maruzen Publishing Co., Ltd., 1978), p. 448; Advance in Polymer Science, 62, 1-48 (1984); New Experimental Chemistry Vol. 14-III (Maruzen Publishing Co., Ltd., 1978), pp. 1838-1846; Organic SulfurChemistry (Synthetic Reaction, 1982, Kagaku-Dojin Publishing Company, INC), chapter 8, pp 237-280; Journal of the Chemical Society of Japan, 87, (5), 74 (1966); JP-A-64-45357, JP-A-61-212554, JP-A-61-100557, JP-A-5-4996, JP-A-7-82244, JP-A-7-82245, JP-A-58-210904 and JP-A-6-184170, first a salt of an onium cation with a halogen ion such as $F^-$, $Cl^-$, $Br^-$ or $I^-$; $OH^-$; $ClO_4^-$; a sulfonate ion such as $FSO_3^-$, $ClSO_3^-$, $CH_3SO_3^-$, $C_6H_5SO_3^-$ or $CF_3SO_3^-$; a sulfate ion such as $HSO_4^-$ or $SO_4^{2-}$; a carbonate ion such as $HCO_3^-$ or $CO_3^{2-}$; a phosphate ion such as $H_2PO_4^-$, $HPO_4^{2-}$ or $PO_4^{3-}$; or the like is produced, and added in a solvent or aqueous solution containing an alkali metal salt, alkali earth metal salt or quaternary ammonium salt that forms an onium salt represented by the formula (1), and other anion components such as $KPF_6$, $KBF_4$ and $LiB(C_6F_5)_4$ as necessary, in a theoretical amount or more, and the mixture is subjected to double decomposition. As a solvent, water or an organic solvent can be used. Examples of the organic solvent include hydrocarbons (hexane, heptane, toluene, xylene and the like), cyclic ethers (tetrahydrofuran, dioxane and the like), chlorinated solvents (chloroform, dichloromethane and the like), alcohols (methanol, ethanol, isopropyl alcohol and the like), ketones (acetone, methyl ethyl ketone, methyl isobutyl ketone and the like), nitriles (acetonitrile and the like) and polar organic solvents (dimethylsulfoxide, dimethylformamide, N-methylpyrrolidone and the like). One of these solvents may be used alone, or two or more thereof may be used in combination.

The aimed photoacid generator thus obtained can be purified by recrystallization or washing with water or a solvent as necessary.

Purification by recrystallization can be performed by dissolving the aimed photoacid generator in a small amount of an organic solvent, and separating the aimed photoacid generator from the organic solvent by precipitating the aimed photoacid generator by adding a poor solvent directly (or after concentration) to an organic solvent solution containing the aimed photoacid generator. Examples of the poor solvent used here include chain ethers (diethyl ether, dipropyl ether and the like), esters (ethyl acetate, butyl acetate and the like), aliphatic hydrocarbons (hexane, cyclohexane and the like) and aromatic hydrocarbons (toluene, xylene and the like). Purification can also be performed utilizing a temperature-dependent difference in solubility. Purification can be performed by recrystallization (a method utilizing difference in solubility in cooling, a method in which a poor solvent is added to precipitate the photoacid generator, or a combination of these methods). In addition, when the photoacid generator is an oil (when photoacid generator is not crystallized), purification can be performed by a method in which the oil is washed with water or a poor solvent.

The structure of the photoacid generator thus obtained can be identified by a general analysis method such as nuclear magnetic resonance spectrum of 1H, $^{13}C$, $^{19}F$, $^{31}P$ and the like, infrared absorption spectrum or elemental analysis.

The photoacid generator may be used in combination with an additional conventionally known photoacid generator other than the above compounds, when needed.

When an additional photoacid generator is contained, the content (% by mole) of the additional photoacid generator is preferably from 0.1 to 100, more preferably from 0.5 to 50, based on the molar number of the photoacid generator of the present invention.

Examples of the additional photoacid generator include conventionally known ones such as onium salts (such as sulfonium, iodonium, selenium, ammonium, phosphonium and the like) and salts of transition metal complex ions with anions.

The photoacid generator may be previously dissolved in a solvent that does not inhibit polymerization, crosslinking reaction and deprotection reaction so that it can be easily dissolved in a composition containing a cationically polymerizable compound.

Examples of the solvent include carbonates such as propylene carbonate, ethylene carbonate, 1,2-butylene carbonate, dimethyl carbonate, diethyl carbonate and the like; ketones such as acetone, methyl ethyl ketone, cyclohexanone, methyl isoamyl ketone, 2-heptanone and the like; polyhydric alcohols and derivatives thereof, such as monomethyl ethers, monoethyl ethers, monopropyl ethers, monobutyl ethers, or monophenyl ethers of ethylene glycol, ethylene glycol monoacetate, diethylene glycol, diethylene glycol monoacetate, propylene glycol, propylene glycol monoacetate, dipropylene glycol, and dipropylene glycol monoacetate; cyclic ethers such as dioxane; esters such as ethyl formate, methyl lactate, ethyl lactate, methyl acetate, ethyl acetate, butyl acetate, methyl pyruvate, methyl acetoacetate, ethyl acetoacetate, ethyl pyruvate, ethyl ethoxyacetate, methyl methoxypropionate, ethyl ethoxypropionate, methyl 2-hydroxypropionate, ethyl 2-hydroxypropionate, ethyl 2-hydroxy-2-methylpropionate, methyl 2-hydroxy-3-methylbutanoate, 3-methoxybutyl acetate, and 3-methyl-3-methoxybutyl acetate; and aromatic hydrocarbons such as toluene and xylene.

When a solvent is used, the amount of the solvent used is preferably from 15 to 1,000 parts by weight, more preferably from 30 to 500 parts by weight, based on 100 parts by weight of the photoacid generator of the present invention. These solvents may be used alone or in combination of two or more.

The photosensitive composition of the present invention comprises the above photoacid generator and a cationically polymerizable compound.

Examples of the cationically polymerizable compound as a constituent of the photosensitive composition include cyclic ethers (such as epoxide, oxetane and the like), ethylenically unsaturated compounds (such as vinyl ether, styrene and the like), bicycloorthoesters, spiroorthocarbonates, spiroorthoesters and the like (such as those described in JP-A No. 11-060996, JP-A No. 09-302269, JP-A No. 2003-026993, JP-A No. 2002-206017, JP-A No. 11-349895, JP-A No. 10-212343, JP-A No. 2000-119306, JP-A No. 10-67812, JP-A No. 2000-186071, JP-A No. 08-85775, JP-A No. 08-134405, JP-A No. 2008-20838, JP-A No. 2008-20839, JP-A No. 2008-20841, JP-A No. 2008-26660, JP-A No. 2008-26644, JP-A No. 2007-277327, "Photopolymer Handbook" edited by The Technical Association of Photopolymers, Japan (1989, Kogyo Chosakai Publishing, Co., Ltd.), "UV/EB Koka Gijutsu" (Technology of UV/EB Curing), edited by Sogo Gijutsu Center (1982, Sogo Gijutsu Center), "UV/EB Koka Zairyo" (UV/EB Curable Materials), edited by RadTech Japan (1992, CMC), "UV-Koka niokeru Koka-Furyo/Sogai-Genin to Sonotaisaku" (Causes of UV Curing Defects/Inhibition and Countermeasures Therefor), edited by TECHNICAL INFORMATION INSTITUTE (2003, TECHNICAL INFORMATION INSTITUTE CO., LTD.), Journal of the Japan Society of Colour Material, 68, (5), 286 to 293 (1995), and Fine Chemical, 29, (19), 5 to 14 (2000) and the like).

Known epoxides and the like may be used as epoxides, examples of which include aromatic epoxides, alicyclic epoxides, and aliphatic epoxides.

Examples of the aromatic epoxides include glycidyl ethers of monohydric or polyhydric phenols having at least one aromatic ring (such as phenol, bisphenol A, phenol novolac, and alkylene oxide adducts thereof).

Examples of the alicyclic epoxides include compounds obtained by epoxidation of compounds having at least one cyclohexene or cyclopentene ring with an oxidizing agent (such as 3,4-epoxycyclohexylmethyl-3,4-epoxycyclohexanecarboxylate and the like).

Examples of the aliphatic epoxides include polyglycidyl ethers of aliphatic polyhydric alcohols or alkylene oxide adducts thereof (such as 1,4-butanediol diglycidyl ether, 1,6-hexanediol diglycidyl ether and the like), polyglycidyl esters of aliphatic polybasic acids (such as diglycidyl tetrahydrophthalate and the like), and epoxidized long-chain unsaturated compounds (such as epoxidized soybean oil, epoxidized polybutadiene and the like).

Known oxetanes and the like may be used as oxetanes, examples of which include 3-ethyl-3-hydroxymethyloxetane, 2-ethylhexyl(3-ethyl-3-oxetanylmethyl)ether, 2-hydroxyethyl(3-ethyl-3-oxetanylmethyl)ether, 2-hydroxypropyl (3-ethyl-3-oxetanylmethyl) ether, 1,4-bis [(3-ethyl-3-oxetanylmethoxy)methyl]benzene, oxetanylsilsesquioxetane, phenol novolac oxetane and the like.

Known cationically polymerizable monomers and the like may be used as ethylenically unsaturated compounds, examples of which include aliphatic monovinyl ethers, aromatic monovinyl ethers, polyfunctional vinyl ethers, styrenes, and cationically polymerizable nitrogen-containing monomers.

Examples of the aliphatic monovinyl ethers include methyl vinyl ether, ethyl vinyl ether, butyl vinyl ether, cyclohexyl vinyl ether and the like.

Examples of the aromatic monovinyl ethers include 2-phenoxyethyl vinyl ether, phenyl vinyl ether, p-methoxyphenyl vinyl ether and the like.

Examples of the polyfunctional vinyl ethers include butanediol-1,4-divinyl ether, triethylene glycol divinyl ether and the like.

Examples of the styrenes include styrene, a-methylstyrene, p-methoxystyrene, p-tert-butoxystyrene and the like.

Examples of the cationically polymerizable nitrogen-containing monomers include vinylmonomers such as N-vinylcarbazole and N-vinylpyrrolidone; and mono- and multifunctional aziridine monomers such as 3-(laziridinyl) ethylpropionate, bis(3-(1-aziridinyl)propionic acid) neopenthylglycol ester, trimethlolpropane tris(3-(2-methyl-1-adiridinyl)propionic acid)ester, pentaerythritol tetrakis(3-(1-adiridinyl)propionic acid)ester and the like.

Examples of the bicycloorthoesters include 1-phenyl-4-ethyl-2,6,7-trioxabicyclo[2.2.2]octane, 1-ethyl-4-hydroxymethyl-2,6,7-trioxabicyclo[2.2.2]octane and the like.

Examples of the spiroorthocarbonates include 1,5,7,11-tetraoxaspiro[5.5]undecane, 3,9-dibenzyl-1,5,7,11-tetraoxaspiro[5.5]undecane and the like.

Examples of the spiroorthoesters include 1,4,6-trioxaspiro [4.4]nonane, 2-methyl-1,4,6-trioxaspiro[4.4]nonane, 1,4,6-trioxaspiro[4.5]decane and the like.

Additional examples of the cationically polymerizable compound include polyorganosiloxanes having at least one cationically polymerizable group in a molecule (such as those described in JP-A 2001-348482, Journal of Polym. Sci., Part A, Polym. Chem., Vol. 28,497 (1990) or the like). These polyorganosiloxanes may be straight chain, branched chain, cyclic, or the mixture of these.

Among these cationically polymerizable compounds, epoxides, oxetanes, and vinyl ethers are preferred, epoxides and oxetane are more preferred, and alicyclic epoxides and oxetanes are particularly preferred. These cationically polymerizable compounds may be used alone or in combination of two or more.

The content of the photoacid generator of the present invention in a photosensitive composition is preferably from 0.05:to 20 parts by weight, more preferably from 0.1 to 10 parts by weight, based on 100 parts by weight of the cationically polymerizable compound. Within the range, the cationically polymerizable compound can be more sufficiently polymerized, so that the physical properties of the cured product can be further improved. It will be understood that the content may be determined taking into account various factors such as the properties of the cationically polymerizable compound, the type (light source, wavelength or the like) and irradiation dose of the light, the temperature, the curing time, the humidity, and the thickness of the coating film, and is not limited to the above range.

The content of the cationically polymerizable compound in the photosensitive composition of the present invention is from 70 to 99.9% by weight, preferably from 80 to 99.5% by weight, more preferably 90 to 99% by weight based on total weight of the photoacid generator and the cationically polymerizable compound. These cationically polymerizable compounds may be used in combination of two or more.

If necessary, the photosensitive composition of the present invention may contain known additives (such as a pigment, a filler, an electroconductive particle, an antistatic agent, a flame retardant, an anti-foaming agent, a fluidity controlling agent, a light stabilizer, an antioxidant, a tack fier, an ion scavenger, an anti-coloring agent, a solvent, a nonreactive resin, a radically polymerizable compound and the like).

The photosensitive composition of the present invention may contain other additives (J) that are generally used for controlling the appearance and physical properties of a cured product of a photosensitive composition. Other additives (J) include a colorant (Ja), metal oxide particles (Jb), metal particles (Jc) and the like.

As the colorant (Ja) in the present invention, pigments such as inorganic pigments and organic pigments, and dyes which have been heretofore used for coating materials, inks and the like can be used.

Examples of the inorganic pigment include chrome yellow, zinc yellow, iron blue, barium sulfate, cadmium red, titanium oxide, zinc white, red oxide, alumina, calcium carbonate, ultramarine blue, carbon black, graphite, titanium black and the like.

Examples of the organic pigment include soluble azo pigments such as β-naphthol systems, β-oxynaphthoic acid-based anilide systems, acetoacetanilide systems, pyrazolone systems and the like; insoluble azo pigments such as β-naphthol systems, β-oxynaphthoic acid systems, β-oxynaphthoic acid-based anilide systems, acetoacetanilide-based monoazo, acetoacetanilide-based disazo, pyrazolone systems and the like; phthalocyanine-based pigments such as copper phthalocyanine blue, halogenated copper phthalocyanine blue, sulfonated copper phthalocyanine blue and metal-free phthalocyanine; and polycyclic or heterocyclic compounds such as isoindolinone systems, quinacridone systems, dioxazine systems, perinone systems, perylene systems and the like.

As specific examples of the dye, examples of the yellow dye include aryl or hetaryl azo dyes having a phenol, a naphthol, an aniline, a pyrazolone, a pyridone or an open chain active methylene compounds as a coupling component; methine dyes such as azomethine dyes, benzylidene dyes and monomethine oxonol dyes: having an open chain active methylene compound as a coupling component; quinone-based dyes such as naphthoquinone dyes and anthraquinone dyes; quinophthalone dyes; nitro and nitroso dyes; acridine dyes; and acridinone dyes.

Examples of the magenta dye include aryl or heteryl azo dyes; having a phenol, a naphthol, an aniline, a pyrazolone, a pyridone, a pyrazolotriazole, a closed ring active methylene compound or a heterocyclic ring (e.g. pyrrole, imidazole, thiophene or thiazole derivative) as a coupling component; methine dyes such as azomethine dyes, arylidene dyes, styryl dyes, merocyanine dyes and oxonol dyes having a pyrazolone or a pyrazolotriazole as a coupling component; carbonium dyes such as diphenylmethane dyes, triphenylmethane dyes and xanthene dyes; quinone-based dyes such as naphthoquinone, anthraquinone and anthrapyridone; and fused polycyclic dyes such as dioxazine dyes.

Examples of the cyan dye include azomethine dyes such as indoaniline dyes and indophenol dyes; polymethine dyes such as cyan ne dyes, oxonol dyes and merocyanine dyes, carbonium dyes such; as diphenylmethane dyes, triphenylmethane dyes and xanthene dyes; phthalocyanine dyes; anthraquinone dyes; aryl or hetaryl azo dyes (C.I. Direct Blue 14 and the like) having a phenol, a naphthol, an aniline, or a pyrrolopyrimidinone or pyrrolotriazinone derivative as a coupling component; and indigo thioindigo dyes.

From the viewpoint of image sharpness of the coating film, the particle diameter of the colorant (Ja) is preferably 0.01 μm to 2.0 μm, more preferably 0.01 μm to 1.0 μm in terms of an average particle diameter.

The addition amount of the colorant (Ja) is not particularly limited, but is preferably 1 to 60% by weight based on the total weight of the photosensitive composition.

When a pigment is used, it is preferable to add a pigment dispersant for improving dispersibility of the pigment and storage stability of the photosensitive composition.

Examples of the pigment dispersant include pigment dispersants (Anti-Terra-U, Disperbyk-101, 103, 106, 110, 161, 162, 164, 166, 167, 168, 170, 174, 182, 184, 2020 and the like) manufactured by BYK Japan K.K.; pigment dispersants (e.g. AJISPER PB 711, PB 821, PB 814, PN 411 and PA 111) manufactured by Ajinomoto Fine-Techno Co., Inc.; and pigment dispersants (e.g. SOLSPERSE 5000, 12000, 32000, 33000, 39000 and the like) manufactured by The Lubrizol Corporation. One of these pigment dispersants may be used alone, or two or more thereof may be used in combination. The addition amount of the pigment dispersant is not particularly limited, but it is preferable that the pigment dispersant is used in an amount ranging from 0.1 to 10% by weight in the photosensitive composition.

Known fillers and the like may be used as fillers, examples of which include fused silica, crystalline silica, calcium carbonate, aluminum oxide, aluminum hydroxide, zirconium oxide, magnesium carbonate, mica, talc, calcium silicate, lithium aluminum silicate and the like.

When a filler is contained, the content of the filler is preferably from 50 to 600,000 parts by weight, more preferably 300 to 200,000 parts by weight, based on 100 parts of the photoacid generator of the present invention.

Known electroconductive particles can be used as electroconductive particles, and metal particles of Ni, Ag, Au, Cu, Pd, Pb, Sn, Fe, Ni, Al and the like, and plated metal particles obtained by further plating the above-mentioned metal particles with a metal, plated resin particles obtained by plating resin particles with a metal, or particles of a substance having conductivity, such as carbon, can be used.

When an electroconductive particle are contained, the content of the electroconductive particle is preferably from 50 to 30000 parts by weight, more preferably from 100 to 20000 parts by weight, based on 100 parts of the photoacid generator.

Known antistatic agents and the like may be used as antistatic agents, examples of which include nonionic antistatic agents, anionic antistatic agents, cationic antistatic agents, ampholytic antistatic agents, and high molecular weight antistatic agents.

When an antistatic agent is contained, the content of the antistatic agent is preferably from 0.1 to 20,000 parts by weight, more preferably from 0.6 to 5,000 parts by weight, based on 100 parts of the photoacid generator of the present invention.

Known flame retardants and the like may be used as flame retardants, examples of which include inorganic flame retardants (such as antimony trioxide, antimony pentoxide, tin oxide, tin hydroxide, molybdenum oxide, zinc borate, barium metaborate, red phosphorus, aluminum hydroxide, magnesium hydroxide, and calcium aluminate); bromine flame retardants (such as tetrabromophthalic anhydride, hexabromobenzene, and decabromobiphenyl ether); and phosphate flame retardants {such as tris(tribromophenyl) phosphate}.

When a flame retardant is contained, the content of the flame retardant is preferably from 0.5 to 40,000 parts by weight, more preferably from 5 to 10,000 parts by weight, based on 100 parts of the photoacid generator of the present invention.

Known anti-foaming agents and the like may be used as anti-foaming agents, examples of which include alcoholic anti-foaming agents, metallic soap anti-foaming agents, phosphate anti-foaming agents, fatty acid ester anti-foaming agents, polyether anti-foaming agents, silicone anti-foaming agents, and mineral oil anti-foaming agents.

Known fluidity controlling agents and the like may be used as fluidity controlling agents, examples of which include hydrogenated castor oil, oxidized polyethylene, organic bentonite, colloidal silica, amide wax, metallic soap, and acrylic ester polymers.

Known light stabilizers and the like may be used as light stabilizers, examples of which include ultraviolet absorbing stabilizers {such as benzotriazole, benzophenone, salicylates, cyanoacrylates, and derivatives thereof}; radical scavenging stabilizers {such as hindered amines}; and quenching stabilizers {such as nickel complexes}.

Known antioxidants and the like may be used as antioxidants, examples of which include phenolic antioxidants (such as monophenolic, bisphenolic, and macromolecular phenolic antioxidants), sulfur-based antioxidants, and phosphorus-based antioxidants.

Known tackifiers and the like may be used as tackifiers, examples of which include coupling agents, silane coupling agents, and titanium coupling agents.

Known ion scavenger and the like may be used as ion scavenger, examples of which include organoaluminum (such as alkoxyaluminum and phenoxyaluminum).

Known anti-coloring agents and the like may be used as anti-coloring agents, and antioxidants are generally effective, examples of which include phenolic antioxidants (such as monophenolic, bisphenolic, and macromolecular phenolic antioxidants), sulfur-based antioxidants, and phosphorus-based antioxidants. However, these anti-coloring agents do not have coloring prevention effect on heat resistance test at high temperature.

When an anti-foaming agent, a fluidity controlling agent, a light stabilizer, an antioxidant, a tackifier, an ion scavenger, or an anti-coloring agent is contained, the content of each material is preferably from 0.1 to 20,000 parts by weight, more preferably from 0.5 to 5,000 parts by weight, based on 100 parts of the photoacid generator of the present invention.

Any solvent that can be used to dissolve the cationically polymerizable compound or to control the viscosity of the photosensitive composition may be used as solvents, examples of which include those listed for the above photoacid generator.

When a solvent is contained, the content of the solvent is preferably from 50 to 2,000,000 parts by weight, more preferably from 200 to 500,000 parts by weight, based on 100 parts of the photoacid generator of the present invention.

Examples of the nonreactive resin include polyester, polyvinyl acetate, polyvinyl chloride, polybutadiene, polycarbonate, polystyrene, polyvinyl ether, polyvinyl butyral, polybutene, hydrogenated styrene-butadiene block copolymers, copolymers of (meth)acrylic acid esters, and polyurethane. The number average molecular weight of these resins is preferably from 1,000 to 500,000, more preferably from 5,000 to 100,000 (the number average molecular weight is a value measured by a general method such as GPC).

When a nonreactive resin is contained, the content of the nonreactive resin is preferably from 5 to 400,000 parts by weight, more preferably from 50 to 150,000 parts by weight, based on 100 parts of the photoacid generator of the present invention.

When a nonreactive resin is contained, it is preferably dissolved in advance in a solvent so that it can be easily dissolved in the cationically polymerizable compound or the like.

Known radically polymerizable compounds and the like may be used as radically polymerizable compounds {such as those described in "Photopolymer Handbook" edited by The Technical Association of Photopolymers, Japan (1989, Kogyo Chosakai Publishing, Co., Ltd.), "UV/EB Koka Gijutsu" (Technology of UV/EB Curing), edited by Sogo Gijutsu Center (1982, Sogo Gijutsu Center), and "UV/EB Koka Zairyo" (UV/EB Curable Materials), edited by RadTech Japan (1992, CMC), examples of which include monofunctional monomers, bifunctional monomers, polyfunctional monomers, epoxy (meth)acrylate, polyester (meth)acrylate, and urethane (meth)acrylate.

When a radically polymerizable compound is contained, the content of the radically polymerizable compound is preferably from 5 to 400,000 parts by weight, more preferably from 50 to 150,000 parts by weight, based on 100 parts of the photoacid generator of the present invention.

When a radically polymerizable compound is contained, a radical polymerization initiator initiating polymerization with heat or light is preferably used so that the compound can be polymerized by radical polymerization.

Known radical polymerization initiators and the like may be used as radical polymerization initiators, examples of which include thermal radical polymerization initiators (such as organic peroxides and azo compounds) and photoradical polymerization initiators (such as acetophenone-based initiators, benzophenone-based initiators, Michler's ketone-based initiators, benzoin-based initiators, thioxanthone-based initiators, and acylphosphine-based initiators.

When a radical polymerization initiator is contained, the content of the radical polymerization initiator is preferably from 0.01 to 20 parts by weight, more preferably from 0.1 to 10 parts by weight, based on 100 parts of the radically polymerizable compound.

The photosensitive composition of the present invention may be prepared by uniformly mixing and dissolving the cationically polymerizable compound, the photoacid generator, and if necessary an optional additive(s) at room temperature (about 20 to 30° C.) or if necessary, under heating (about 40 to 90° C.), or by further kneading them with a triple-roll mill or the like.

For the photosensitive composition of the present invention, a light source can be used which includes an argon ion laser, a helium cadmium laser, a helium neon laser, a krypton ion laser, various kinds of semiconductor lasers, a xenon lamp or an LED light source, and is capable of radiating an energy ray in a visible to infrared region. Depending on a use, a high-pressure mercury lamp that is commonly used, as well as an ultra-high-pressure mercury lamp, a metal halide lamp and a high power metal halide lamp can be used because an energy ray is generated even at a wavelength of 400 nm or more.

While the light irradiation time is influenced by the intensity of the light source or the light transparency to the photosensitive composition, the light exposure time of about 0.1 to 10 seconds is enough at room temperature (about 20 to 30° C.). However, if the light transparency is low or if the thickness of the photosensitive composition is large, for example, it is sometimes preferred to spend more time. Most photosensitive compositions are cured by cationic polymerization in 0.1 seconds to several minutes after the light irradiation. If necessary, however, post-curing may be performed by heating at a temperature of room temperature (about 20 to 30° C.) to 200° C. for several seconds to several hours after the light irradiation.

As a method for applying the photosensitive composition of the present invention to a base material, a known coating method such as spin coating, roll coating or spray coating, as well as a known printing method such as lithographic printing, carton printing, metal printing, offset printing, screen printing or gravure printing can be used. The photosensitive composition can be also applied by inkjet-type coating in which fine droplets are continuously discharged.

EXAMPLES

Hereinafter, the present invention is more specifically described with reference to examples, which however are not intended to limit the invention. "%" means "% by weight" unless otherwise specified.

Production Example 1, Synthesis of Metal Complex Precursor (a-1)

Synthesis of octaethylporphyrinatesilicon (IV) dichloride (a-1)

The compound (a-1) was synthesized by reaction of octaethylporphyrin and tetrachlorosilane in accordance with J. W; Buchiler, et. al., Chem. Ber. 1973, 106, 2710.

Production Example 2, Synthesis of Metal Complex Precursor (a-3)

Synthesis of dichlorotetraphenylporphyrinateantimony(V)bromide (a-3)

The compound (a-3) was synthesized by reaction of tetraphenylporphyrin and antimony trichloride in accordance with Y. M. Idemori, et. al., Journal of Biological Inorganic Chemistry, 2015, 20, 771.

Production Example 3, Synthesis of Metal Complex Precursor (a-6)

Synthesis of tetrakis(pentafluorophenyl)porphyrinatesilicon(IV)dichloride

The compound (a-6) was synthesized as in Production Example 1, except that "octaethylporphyrin" was replaced with "tetrakis(pentafluorophenyl)porphyrin".

Production Example 4, Synthesis of Metal Complex Precursor (a-8)

Synthesis of phthalocyanategermanium(IV) dichloride

In a reaction vessel, 150 g of n-pentanol, 23 g of 1,2-dicyanobenzene and 10 g of germanium tetrachloride were added, and 27 g of DBU (1,8-diazabicyclo[5,4,0]-7-undecene) was added and mixed. The reaction mixture was heated to 140° C. and allowed to react under reflux for 12 hours, and cooled to room temperature. The reaction solution was added dropwise while stirring to 1500 g of methanol/water=1/2 (weight ratio) to obtain a slurry. The slurry was filtered. The residue was washed with 100 g of methanol/water=1/2 (weight ratio) five times and dried to obtain 18.9 g of an aimed product. It was confirmed by $^{1}$H-NMR that this dark blue solid product was metal complex precursor (a-8)

The structures of the above metal complex precursor (a) are shown below. All metal complex precursors except the above synthesized products are reagents by Aldrich Corporation.

[Chemical Formula 10]

(a-1)

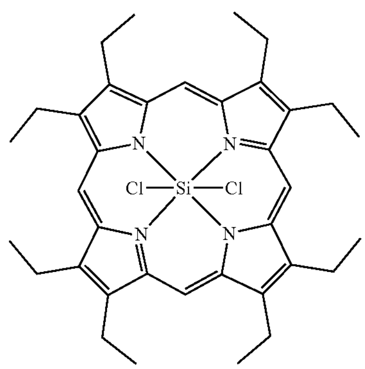

(a-2)

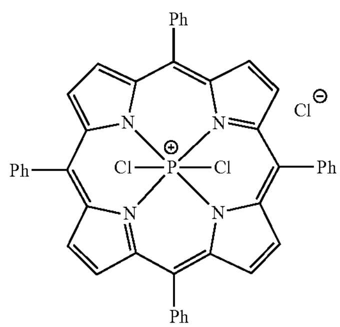

(a-3)

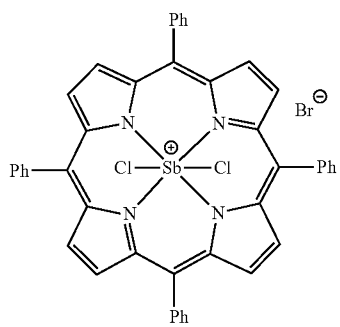

-continued (a-4)

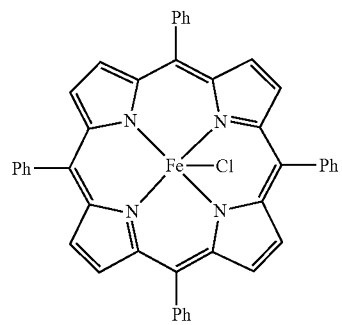

(a-5)

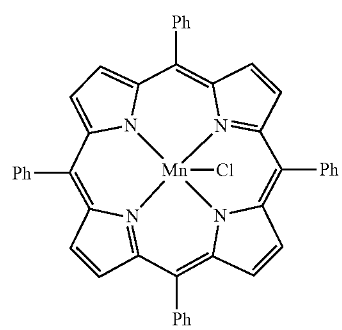

(a-6)

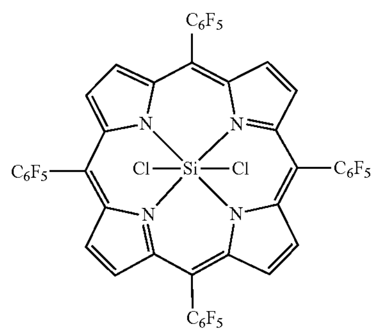

(a-7)

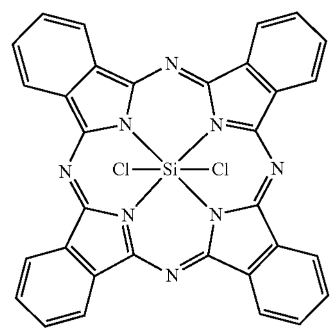

(a-8)

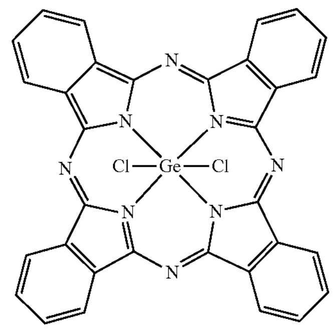

-continued (a-9)

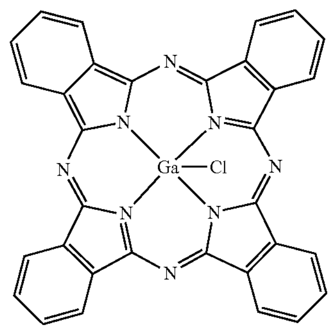

(a-10)

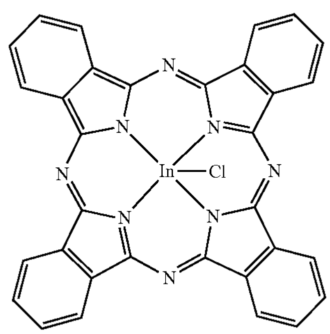

(a-11)

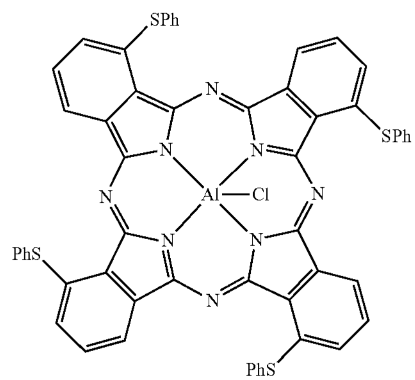

(a-12)

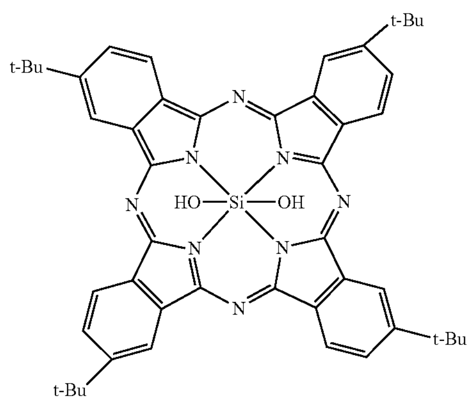

-continued (a-13)

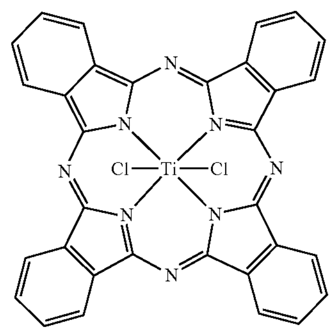

(a-14)

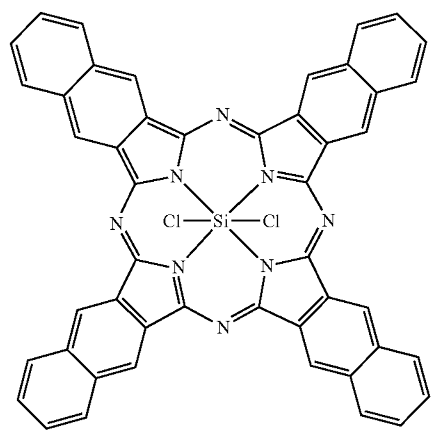

(a-15)

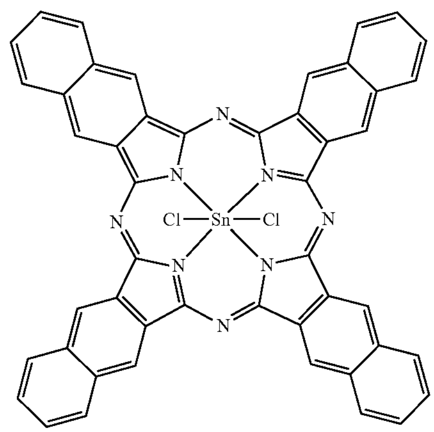

Production Example 5, Synthesis of Axial Ligand Precursor (b-1/$PF_6$)

(1) Intermediate-1 (b-1/Cl): Synthesis of 3,5-dimethyl-4-hydroxyphenyldiphenylsulfoniumchloride Salt In a reaction vessel, 7.3 g of 2,6-dimethylphenol, 50 g of methanesulfonic acid and 7 g of phosphorus pentaoxide were added, and mixed. Then, 10 g of diphenylsulfoxide was added there, and allowed to react at 45° C. for 6 hours. The reaction solution was added gradually while stirring to 100 mL of 20% saline water while cooling with ice bath. Then, 100 mL of dichloromethane was added in addition to the reaction solution and stirred for one hour. The operation of allowing the solution to stand still and then removing the water layer by liquid separation was performed. The organic layer was washed with 50 ml of water five times, and concentrated. By recrystallization with acetone, 15.2 g of white solid was obtained. It was confirmed by 1H-NMR that this white solid product was (b-1/Cl).

(2) Synthesis of Axial Ligand Precursor (b-1/$PF_6$)

In a reaction vessel, 4.3 g of (b-1/Cl), 20 ml of THF, 1.5 g of potassium carbonate and 1.7 g of 2-(2-hydroxyethoxy) ethylbromide were added, and allowed to react at 60° C. for 6 hours. After reaction, the reaction solution was added to an aqueous solution dissolved 2.0 g of $KPF_6$ in 50 mL of water. The mixed solution was stirred for one hour, and extracted with 100 mL of dichloromethane. Then, the operation of removing the water layer by liquid separation was performed. The organic layer was washed with 50 mL of water five times, and concentrated. By recrystallization with dichloromethane-hexane, 3.2 g of white solid was obtained (yield 60%). It was confirmed by $^{1}H^{-}$, $^{19}F^{-}$, $^{31}P$-NMR that this white solid product was axial ligand precursor (b-1/$PF_6$).

Production Example 6, Synthesis of Axial Ligand Precursor (b-1/$SbF_6$)

6.3 g of white solid was obtained (yield 72%) as in Production Example 5 (2), except that "2.0 g of $KPF_6$" was replaced with "3.1 g of $KSbF_6$". It was confirmed by $^{1}H$-, $^{19}F$-NMR that this white solid product was axial ligand precursor (b-1/$SbF_6$).

Production Example 7, Synthesis of Axial Ligand Precursor (b-1'/B ($C_6F_5$) 4)

6.3 g of pale yellow solid was obtained (yield 59%) as in Production Example 5 (2), except that "2.0 g of $KPF_6$" was replaced with "7.7 g of $NaB(C_6F_5)_4$ (dissolved in 100 mL of water)". It was confirmed by 1H-, $^{19}F$-NMR that this pale yellow solid product was axial ligand precursor (b-1/B ($C_6F_5$) 4).

Production Example 8, Synthesis of Axial Ligand Precursor (b-1/$(C_2F_5)_3PF_3$)

5.1 g of pale yellow solid was obtained (yield 61%) as in Production Example 5(2), except that "2.0 g of $KPF_6$" was replaced with "5.3 g of $K(C_2F_5)_3PF_3$". It was confirmed by $^{1}H$-, $^{19}F$—, $^{31}P$-NMR that this pale yellow solid product was axial ligand precursor (b-1/$(C_2F_5)_3PF_3$).

Production Example 9, Synthesis of Axial Ligand Precursor (b-1/Ga ($C_6F_5$) 4)

6.2 g of white solid was obtained (yield 55%) as in Production Example 5 (2), except that "2.0 g of $KPF_6$" was replaced with "8.4 g of NaGa $(C_6F_5)_4$ (dissolved in 100 mL of water)". It was confirmed by $^{1}H$-, $^{19}F$-NMR that this white solid product was axial ligand precursor (b-1/Ga $(C_6F_5)_4$).

Production Example 10, Synthesis of Axial Ligand Precursor (b-1/Al (Ot-$C_4F_9)_4$)

6.0 g of white solid was obtained (yield 44%) as in Production Example 5 (2), except that "2.0 g of $KPF_6$" was replaced with "10.7 g of LiAl $(O^t—C_4F_9)_4$ (dissolved in 100 mL of water)". It was confirmed by $^{1}H$—, $^{19}F$-NMR that this white solid product was axial ligand precursor (b-1/Al (Ot-$C_4F_9)_4$).

Production Example 11, Synthesis of Axial Ligand Precursor (b-1/C ($CF_3SO_2$) 3)

4.9 g of white solid was obtained (yield 61%) as in Production Example 5 (2), except that "2.0 g of $KPF_6$" was replaced with "4.9 g of $KC(CF_3SO_2)_3$". It was confirmed by $^{1}H$—, $^{19}F$-NMR that this white solid product was axial ligand precursor (b-1/C $(CF_3SO_2)_3$).

Production Example 12, Synthesis of Axial Ligand Precursor (b-2/$PF_6$)

(1) Intermediate-2: Synthesis of 4-(3-(hydroxydimethylsilyl)propyl)phenyldiphenylsulfoniumtr iflate (b-2/OTf)

In a reaction vessel, 8.1 g of diphenylsufoxide and 100 mL of dichloromethane were added, and cooled to −10° C. with ice bath. Then, 13.0 g of trifluoromethanesulfonic anhydride was added dropwise there by not exceeding 0° C., and 8.8 g of 3-(ethoxydimethylsilyl)propylbenzene was added dropwise in addition at 0° C. or less. Then, the reaction solution was heated gradually to room temperature, and stirred for one hour at room temperature. The reaction solution was added dropwise to 50 mL of 5% sodium hydrogen carbonate aqueous solution cooled with ice bath while stirring. The operation of allowing the solution to stand still and then removing the water layer by liquid separation was performed. The organic layer was washed with 50 mL of water five times, and concentrated. By recrystallization of the obtained crude crystal with dichloromethane-cyclohexane, 12.1 g of pale yellow solid was obtained. It was confirmed by 1H-NMR that this pale yellow solid product was (b-2/OTf).

(2) Synthesis of Axial Ligand Precursor (b-2/$PF_6$)

In a reaction vessel, 5.3 g of (b-2/OTf) was added, and dissolved with 100 mL of dichloromethane. The reaction solution was added to an aqueous solution dissolved 2.0 g of $KPF_6$ in 50 mL of water, and stirred for 6 hours. Then, the operation of removing the water layer by liquid separation was performed. The organic layer was washed with 50 mL of water five times, and concentrated. By recrystallization with dichloromethane-hexane, 3.4 g of pale yellow solid was obtained (yield 65%). It was confirmed by $^{1}H$-, $^{19}F$-, $^{31}P$-NMR that this pale yellow solid product was axial ligand precursor (b-2/$PF_6$).

Production Example 13, Synthesis of Axial Ligand Precursor (b-2/$(C_2F_5)_3PF_3$)

4.9 g of pale yellow solid was obtained (yield 58%) as in Production Example 12(2), except that "2.0 g of $KPF_6$" was replaced with "5.3 g of K $(C_2F_5)_3PF_3$)". It was confirmed by $^{1}H$-, $^{19}F$-, $^{31}P$-NMR that this pale yellow solid product was axial ligand precursor (b-2/$(C_2F_5)_3PF_3$).

Production Example 14, Synthesis of Axial Ligand Precursor (b-2/$SbF_6$)

4.2 g of pale yellow solid was obtained (yield 68%) as in Production Example 12(2), except that "2.0 g of $KPF_6$" was replaced with "3.1 g of $KSbF_6$". It was confirmed by $^1H$-, $^{19}F$-NMR that this pale yellow solid product was axial ligand precursor (b-2/$SbF_6$).

Production Example 15, Synthesis of Axial Ligand Precursor (b-3/Ga $(C_6F_5)_4$)

(1) Intermediate-3: Synthesis of 4-carboxyphenyldiphenylsulfoniumtriflate

In a reaction vessel (A), 10 g of 4-iodobenzoic acid was added, and dissolved with 150 mL of THF. 1.8 g of sodium hydride was added there. The reaction solution was cooled to −40° C. after stirring for 10 minutes. Then, 30 mL of 15% diisopropylmagnesiumbromide THF solution was added dropwise there, and stirred at −10° C. for 3 hours.

In another reaction vessel (B), 16 g of diphenylsulfoxide was added, and dissolved with 50 mL of THF. The reaction solution was cooled to −40° C., and 15 g of trimethylsilyl trifluoromethanesulfonate was added dropwise there. The reaction solution was stirred at −40° C. for 30 minutes, and added to reaction vessel (A) through a tube. The reaction solution was stirred at −20° C. for 3 hours, and cooled to −70° C. 100 mL of 40% hydrogen bromide aqueous solution was added there. The reaction mixture was heated to room temperature, and 300 mL of diethylether and 200 mL of 40% hydrogen bromide aqueous solution was added there. The reaction mixture was stirred for one hour, and allowed to stand still. After liquid separation, the water layer was extracted with diethylether and dichloromethane. The extract together with the organic layer was concentrated. Then the concentrate was purified by silica gel column chromatography, so that 15 g of white solid was obtained. It was confirmed by 1H-NMR that this white solid product was Intermediate-3.

(2) Intermediate-4: Synthesis of 4-[N-{(3-(dimethylhydroxysilyl) propyl)}carbamoyl]phenyldiphenylsulfoniumtriflate (b-3/OTf)

[Chemical Formula 11]

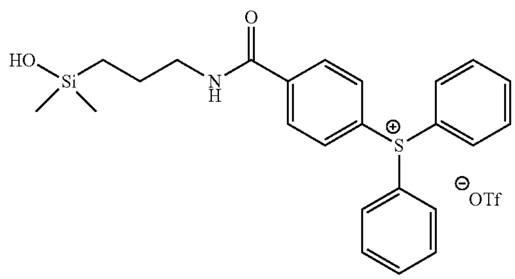

In a reaction vessel, 4.5 g of Intermediate-3 and 30 mL of DMF were added, and 3.8 g of 1-ethyl-3-(3-dimethylaminopropyl) carbodiimide hydrochlonic acid salt was added there in addition. The reaction solution was stirred for one hour, and 1.5 g of 3-aminopropyldimethylethoxysilane was added dropwise there. Then the reaction solution was stirred for 12 hours, and added to 100 mL of water. The reaction mixture was extracted with 50 mL of dichloromethane. The organic layer was washed with 1N hydrochlonic acid and washed with water five times, and concentrated. The obtained crude crystal was used as Intermediate-4. It was confirmed by 1H-NMR that the main ingredient of the crude crystal product was Intermediate-4 (b-3/OTf).

(3) Axial Ligand Precursor (b-3/Ga $(C_6F_5)_4$)

6.3 g of pale yellow solid was obtained (yield 54%) as in Production Example 12(2), except that "5.3 g of (b-2/OTf)" was replaced with "5.7 g of (b-3/OTf)" and "2.0 g of $KPF_6$" was replaced with "8.4 g of $NaGa(C_6F_5)_4$ (dissolved in 100 mL of water)". It was confirmed by 1H-, $^{19}F$-, $^{31}P$-NMR that this pale yellow solid product was axial ligand precursor (b-3/Ga $(C_6F_5)_4$).

Production Example 16, Synthesis of Axial Ligand Precursor (b-4/B $(C_6F_5)$ 4)

(1) Intermediate-5: Synthesis of (3-phenylpropynyl) dimethylethoxysilane

In a reaction vessel, 6.4 g of dimethylethoxyethynylsilane and 500 mL of THF were added, and cooled to −78° C. Then, 37 mL of 15% n-butyllithium-hexane solution was added dropwise there. The reaction solution was stirred for one hour, and 9.4 g of benzylbromide (diluted with 50 mL of THF) was added dropwise there. Then the reaction solution was heated to room temperature, and stirred for 6 hours in addition. 30 mL of 10% ammonium chloride aqueous solution was added slowly to stop the reaction. The reaction solution was added to 400 mL of water. The reaction mixture was extracted with 100 mL of diethylether five times. The organic layer was washed with water three times. The organic layer was concentrated by evaporator, and 9.5 g of yellow oily product was obtained. The obtained yellow oily product was used as Intermediate-5. It was confirmed by $^1H$-NMR that the main ingredient of the product was Intermediate-5.

(2) Intermediate-6: Synthesis of 4-{3-(hydroxydimethylsilyl)-1-propynyl}phenyldiphenylsulfon iumtriflate (b-4/OTf)

10.8 g of pale yellow solid was obtained as in Production Example 12(1), except that "8.8 g of 3-(ethoxydimethylsilyl) propylbenzene" was replaced with "8.7 g of Intermediate-5". It was confirmed by $^1H$-NMR that this pale yellow solid product was (b-4/OTf).

(3) Axial Ligand Precursor (b-4/$B(C_6F_5)_4$)

10.8 g of pale yellow solid was obtained as in Production Example 12(2), except that "5.3 g of (b-2/OTf)" was replaced with "5.2 g of (b-4/OTf)" and "2.0 g of $KPF_6$" was replaced with "7.7 g of $NaB(C_6F_5)_4$ (dissolved in 100 mL of water)". It was confirmed by $^1H$-NMR that this pale yellow solid product was axial ligand precursor (b-4/B $(C_6F_5)$ 4).

Production Example 17, Synthesis of Axial Ligand Precursor (b-5/Ga $(C_6F_5)_4$)

(1) Intermediate-7: Synthesis of (3-carboxypropyl-1-on-phenyl) diphenylsulfonium chloride In a reaction vessel, 9.0 g of triphenylsulfonium chloride, 50 mL of dichloromethane and 4.0 g of aluminum chloride were added, and stirred. The reaction solution was cooled with ice bath, and 9.0 g of succinic anhydride was added dropwise there. Then, the reaction solution was stirred at room temperature for 8 hours, and added to 100 mL of ice-water. In addition, 50 mL of dichloromethane was added there. The reaction mixture was stirred for one hour. The operation of allowing the reaction mixture to stand still and then removing the water layer was performed. The organic layer was washed with 50 mL of water five times, and concentrated. Then the concentrate was purified by silica gel column chromatography, so that 13.8 g of white solid was obtained. It was confirmed by $^1$H-NMR that this white solid product was Intermediate-7.

(2) Intermediate-8: Synthesis of (b-5/Cl)

[Chemical Formula 12]

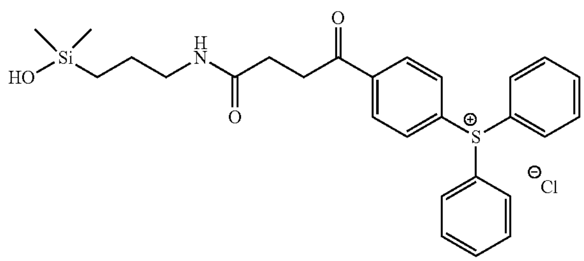

Crude crystal product was obtained as in Production Example 15(2), except that "4.5 g of Intermediate-3" was replaced with "4.0 g of Intermediate-7". It was confirmed by 1H-NMR that the main ingredient of the product was Intermediate-8 (b-5/Cl).

(3) Axial Ligand Precursor (b-5/Ga $(C_6F_5)_4$)

7.3 g of pale yellow solid was obtained (yield 60%) as in Production Example 12(2), except that "5.3 g of (b-2/OTf)" was replaced with "5.1 g of (b-5/Cl)" and "2.0 g of $KPF_6$" was replaced with "8.4 g of $NaGa(C_6F_5)_4$ (dissolved in 100 mL of water)". It was confirmed by $^1$H-, $^{19}$F-NMR that this pale yellow solid product was axial ligand precursor (b-5/Ga$(C_6F_5)_4$).

Production Example 18, Synthesis of Axial Ligand Precursor (b-6/$(C_2F_5)_3PF_3$)

(1) Intermediate-9: Synthesis of 4-(4-phenyl-1,3-butadiynyl)phenyldimethylethoxysilane In a reaction vessel, 2.8 g of 4-(4-phenyl-1,3-butadiynyl)-1-bromobenzene and 20 mL of THF were added, dissolved, and cooled to −78° C. Then, 8 mL of 15% n-butyllithium-hexane solution was added dropwise there. The reaction solution was stirred for one hour, and 1.4 g of chlorodimethylethoxysilane (diluted with 10 mL of THF) was added dropwise there. Then the reaction solution was heated to room temperature, and stirred for 6 hours in addition. 20 mL of 10% ammonium chloride aqueous solution was added slowly at ice cold temperature to the reaction solution, and stirred. The reaction mixture was extracted with 50 mL of hexane. The organic layer was washed with water three times. The organic layer was concentrated by evaporator, and 2.8 g of yellow oily product was obtained. The obtained yellow oily product was used as Intermediate-9. It was confirmed by 1H-NMR that the main ingredient of the product was Intermediate-9.

(2) Intermediate-10: Synthesis of 4-({4-(p-dimethylhydroxysilyl)phenyl-1,3-butadiynyl}phenyldi phenylsulfoniumtriflate (b-6/OTf)

12.8 g of pale yellow solid was obtained as in Production Example 12(1), except that "8.8 g of 3-(ethoxydimethylsilyl) propylbenzene" was replaced with "12.2 g of Intermediate-9". It was confirmed by $^1$H-NMR that this pale yellow solid product was (b-6/OTf).

(3) Axial Ligand Precursor (b-6/$(C_2F_5)_3PF_3$)

6.4 g of pale yellow solid was obtained as in Production Example 12(2), except that "5.3 g of (b-2/OTf)" was replaced with "6.1 g of (b-6/OTf)" and "2.0 g of $KPF_6$" was replaced with "5.3 g of K $(C_2F_5)_3PF_3$". It was confirmed by $^1$H-, $^{19}$F-, $^{31}$P-NMR that this pale yellow solid product was axial ligand precursor (b-6/$(C_2F_5)_3PF_3$)

Production Example 19, Synthesis of Axial Ligand Precursor (b-7/Ga $(C_6F_5)_4$)

(1) Intermediate-11: Synthesis of biphenyldimethylethoxysilane 2.4 g of pale yellow oily product was obtained as in Production Example 17(1), except that "2.8 g of 4-(4-phenyl-1,3-butadiynyl)-1-bromobenzene" was replaced with "2.3 g of 4-bromobiphenyl". The obtained yellow oily product was used as Intermediate-11. It was confirmed by $^1$H-NMR that the main ingredient of the product was Intermediate-11.

(2) Intermediate-12: Synthesis of 4-{4'-(dimethlhydroxysilyl)phenyl}phenyldiphenylsulfoniumtr iflate (b-7/OTf)

15.8 g of white solid was obtained as in Production Example 12(1), except that "8.8 g of 3-(ethoxydimethylsilyl) propylbenzene" was replaced with "10.3 g of Intermediate-11". It was confirmed by $^1$H-NMR that this white solid product was (b-7/OTf).

(3) Axial Ligand Precursor (b-7/Ga$(C_6F_5)_4$)

7.0 g of pale yellow solid was obtained as in Production Example 12(2), except that "5.3 g of (b-2/OTf)" was replaced with "6.1 g of (b-7/OTf)" and "2.0 g of $KPF_6$" was replaced with "8.4 g of $NaGa(C_6F_5)_4$ (dissolved in 100 mL of water)". It was confirmed by 1H-, $^{19}$F-NMR that this pale yellow solid product was axial ligand precursor (b-7/Ga $(C_6F_5)_4$).

Production Example 20, Synthesis of Axial Ligand Precursor (b-8/$(C_2F_5)_3PF_3$)

(1) Intermediate-13: Synthesis of 4-(ethoxydimethylsilyl)stilbene 2.7 g of pale yellow oily product was obtained as in Production Example 18(1), except that "2.8 g of 4-(4-phenyl-1,3-butadiynyl)-1-bromobenzene" was replaced with "2.6 g of 4-bromostilbene". The obtained yellow oily product was used as Intermediate-13. It was confirmed by $^{1}$H-NMR that the main ingredient of the product was Intermediate-13.

(2) Intermediate-14: Synthesis of 4-[1-(p-(dimethylhydroxysilyl)phenyl)ethenyl]phenyldiphenyl sulfoniumtriflate (b-8/OTf)

14.1 g of pale yellow solid was obtained as in Production Example 12(1), except that "8.8 g of 3-(ethoxydimethylsilyl) propylbenzene" was replaced with "11.3 g of Intermediate-13". It was confirmed by 1H-NMR that this pale yellow solid product was (b-8/OTf).

(3) Axial Ligand Precursor (b-8/$(C_2F_5)_3PF_3$)

5.2 g of pale yellow solid was obtained as in Production Example 12(2), except that "5.3 g of (b-2/OTf)" was replaced with "5.9 g of (b-8/OTf)" and "2.0 g of $KPF_6$" was replaced with "5.3 g of K $(C_2F_5)_3PF_3$". It was confirmed by $^{1}$H-, $^{19}$F-, $^{31}$P-NMR that this pale yellow solid product was axial ligand precursor (b-8/$(C_2F_5)_3PF_3$)

Production Example 21, Synthesis of Axial Ligand Precursor (b-9-/Al $(O^t\text{-}C_4F_9)_4$)

(1) Intermediate-15: Synthesis of (2-methoxy-4-hydroxyphenyl)phenyliodonium chloride In a reaction vessel, 22 g of iodosylbenzene, 12.4 g of 3-methoxyphenol, 700 g of acetic acid and 70 g of acetic anhydride were added, and cooled with ice bath. Then, 12 g of concentrated sulfuric acid was added dropwise there by not exceeding 5° C., and allowed to react at room temperature for 3 hours. Then, the reaction solution was added dropwise gradually to 200 mL of 20% saline water while stirring and cooling with ice bath. In addition, 100 mL of dichloromethane was added to the reaction mixture solution, and stirred for one hour. The operation of allowing the solution to stand still and then removing the water layer by liquid separation was performed. The organic layer was washed with 50 mL of water five times, and concentrated. Then the concentrate was purified by column chromatography, so that 10.3 g of white solid was obtained. It was confirmed by $^{1}$H-NMR that this white solid product was Intermediate-15.

(2) Intermediate-16: Synthesis of {2-methoxy-4-(2-hydroxyethoxy)ethyl}phenylphenyliodonium chloride (b-9/Cl)

In a reaction vessel, 3.3 g of Intermediate-15, 20 mL of THF, 1.5 g of potassium carbonate and 1.7 g of 2-(2-hydroxyethoxy)ethyl bromide were added, and allowed to react at room temperature for 18 hours. The reaction solution was concentrated by evaporator, and the obtained oily product was dissolved with 50 mL of dichloromethane. The organic layer was washed with 50 mL of water five times, and concentrated. By recrystallization with dichloromethane-hexane, 3.8 g of white solid was obtained. It was confirmed by 1H-NMR that this white solid product was (b-9/Cl).

(3) Axial Ligand Precursor (b-9/Al $(Ot\text{-}C_4F_9)_4$)

7.6 g of pale yellow solid was obtained (yield 55%) as in Production Example 12(2), except that "5.3 g of (b-2/OTf)" was replaced with "4.5 g of (b-9/Cl)" and "2.0 g of $KPF_6$" was replaced with "10.7 g of $LiAl(Ot\text{-}C_4F_9)_4$(dissolved in 100 mL of water)". It was confirmed by $^{1}$H-, $^{19}$F-NMR that this pale yellow solid product was axial ligand precursor (b-9/Al $(Ot\text{-}C_4F_9)_4$).

Production Example 22, Synthesis of Axial Ligand Precursor (b-9/$(C_2F_5)_3PF_3$)

5.2 g of pale yellow solid was obtained (Yield 61%) as in Production Example 12(2), except that "5.3 g of (b-2/OTf)" was replaced with "4.5 g of (b-9/Cl)" and "2.0 g of $KPF_6$" was replaced with "5.3 g of $K(C_2F_5)_3PF_3$". It was confirmed by 1H-, $^{19}$F-, $^{31}$P-NMR that this pale yellow solid product was axial ligand precursor (b-9/$(C_2F_5)_3PF_3$).

Production Example 23, Synthesis of Axial Ligand Precursor (b-9/$Ga(C_6F_5)_4$)

5.5 g of pale yellow solid was obtained (Yield 48%) as in Production Example 12(2), except that "5.3 g of (b-2/OTf)" was replaced with "4.5 g of (b-9/Cl)" and "2.0 g of $KPF_6$" was replaced with "8.4 g of $NaGa(C_6F_5)_4$ (dissolved in 100 mL of water)". It was confirmed by 1H-, $^{19}$F-NMR that this pale yellow solid product was axial ligand precursor (b-9/$Ga(C_6F_5)_4$).

Production Example 24, Synthesis of Axial Ligand Precursor (b-9/B $(C_6F_5)_4$)

5.8 g of pale yellow solid was obtained (Yield 53%) as in Production Example 12(2), except that "5.3 g of (b-2/OTf)" was replaced with "4.5 g of (b-9/Cl)" and "2.0 g of $KPF_6$" was replaced with "7.7 g of NaB $(C_6F_5)_4$ (dissolved in 100 mL of water)". It was confirmed by 1H-, $^{19}$F-NMR that this pale yellow solid product was axial ligand precursor (b-9/B $(C_6F_5)_4$).

Production Example 25, Synthesis of Axial Ligand Precursor (b-10/Al $(Ot\text{-}C_4F_9)$ 4)

(1) Intermediate-17: Synthesis of (2,6-dimethoxy-4-hydroxyphenyl)phenyliodonium chloride 29.5 g of white solid was obtained as in Production Example 21 (1), except that "12.4 g of 3-methoxyphenol" was replaced with "15.4 g of 3,5-dimethoxyphenol". It was confirmed by 1H-NMR that this white solid product was Intermediate-17.

(2) Axial Ligand Precursor (b-10/Al $(O^t\text{-}C_4F_9)_4$)

In a reaction vessel, 3.6 g of Intermediate-17, 20 mL of THF, 1.5 g of potassium carbonate and 2.1 g of 2-(2-hydroxyethbxyethoxy)ethyl bromide were added, and allowed to react at room temperature for 18 hours. The reaction solution was added to an aqueous solution of 10.7 g of LiAl $(O^t\text{—}C_4F_9)_4$ dissolved in 100 mL of water, and stirred for one hour. The reaction mixture was extracted with 50 mL of dichloromethane. Then, the water layer was removed by liquid separation. The organic layer was washed with 50 mL of water five times, and concentrated. By recrystallization with dichloromethane-hexane, 7.6 g of pale yellow solid was obtained (Yield 52%). It was confirmed by 1H-, $^{19}$F-NMR that this pale yellow solid product was axial ligand precursor Production Example 26, Synthesis of Axial Ligand Precursor (b-11/$(C_2F_5)_3PF_3$)

In a reaction vessel, 2.6 g of 4-t-butyliodobenzene, 3.3 g of 3-(ethoxydimethylsilyl)propylbenzene, 30 mL of dichloromethane and 50 mL of trifluoroacetic acid were added, and dissolved. The reaction solution was heated to 40° C., and 2.7 g of potassium peroxymonosulfate was added gradually to the reaction solution. After allowing to react for 20 hours, the reaction solution was added to 100 mL of cold water. 100 mL of dichloromethane was added there, and stirred for one hour. The operation of allowing the solution to stand still and then removing the water layer by liquid separation was performed. The organic layer was added to an aqueous solution of 5.3 g of K $(C_2F_5)_3PF_3$ dissolved in 50 mL of water, and stirred for one hour. The operation of allowing the solution to stand still and then removing the water layer by liquid separation was performed. The organic layer was washed with 50 mL of water five times, and concentrated. Then the obtained oily product was purified by dichloromethane-cyclohexane, so that 4.5 g of pale yellow solid product was obtained (Yield 47%). It was confirmed by $^1$H-, $^{19}$F-, $^{31}$P-NMR that this pale yellow solid product was axial ligand precursor (b-11/$(C_2F_5)_3PF_3$).

Production Example 27, Synthesis of Axial Ligand Precursor (b-12/$(C_2F_5)_3PF_3$)

(1) Intermediate-18: Synthesis of (4-carboxyphenyl):(4-t-amylphenyl)iodoniumtriflate In a reaction vessel, 2.5 g of 4-iodobenzoic acid and 3.3 g of m-chloroperbenzoic acid (65%) were added, and dissolved with 30 mL of dichloromethane. 1.6 g of t-amylbenzene was added there. The reaction solution was cooled to 0° C., and 3.0 g of trifluoromethanesulfonic acid was added dropwise there by not exceeding 5° C. The reaction solution was heated to room temperature gradually, and stirred at room temperature for 2 hours. The reaction solution was concentrated under reduced pressure, and 50 mL of diethylether was added there. The reaction solution was allowed to stand still at −10° C. and precipitate solid product. By filtration, 3.5 g of white solid product was obtained. It was confirmed by 1H-NMR that this white solid product was Intermediate-18.

(2) Intermediate-19: Synthesis of (b-12/OTf)

[Chemical Formula 13]

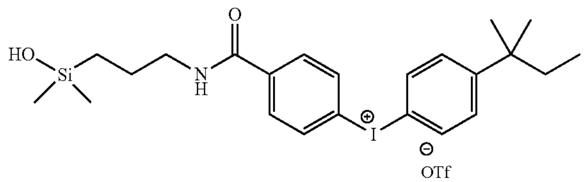

Intermediate-19 was obtained as in Production Example 15(2), except that "4.5 g of Intermediate-3" was replaced with "5.4 g of Intermediate-18". It was confirmed by 1H-NMR that the main ingredient of the product was Intermediate-19 (b-12/OTf).

(3) Axial Ligand Precursor (b-12/$(C_2F_5)_3PF_3$)

5.6 g of pale yellow solid was obtained (Yield 59%) as in Production Example 12(2), except that "5.3 g of (b-2/OTf)" was replaced with "6.6 g of (b-12/OTf)" and "2.0 g of $KPF_6$" was replaced with "5.3 g of $K(C_2F_5)_3PF_3$". It was confirmed by $^1$H-, $^{19}$F-, $^{31}$P-NMR that this pale yellow solid product was axial ligand precursor (b-12/$(C_2F_5)_3PF_3$).

Production Example 28, Synthesis of Axial Ligand Precursor (b-13/$(C_2F_5)_3PF_3$)

(1) Intermediate-20: Synthesis of 4-(hydroxyethoxy)ethyl-2,6-methoxyaniline

In a reaction vessel, 1.7 g of 2,6-dimethoxy-4-hydroxyaniline, 20 mL of THF, 1.5 g of potassium carbonate and 1.7 g of 2-(2-hydroxyethoxy)ethyl bromide were added, and allowed to react at 60° C. for one hour. The reaction solution was concentrated by evaporator, and 10 mL of dichloromethane was added there. The organic layer was washed with water five times, and concentrated, and 2.2 g of pale yellow oily product was obtained. It was confirmed by $^1$H-NMR that this pale yellow oily product was Intermediate-20.

(2) Axial Ligand Precursor (b-13/$(C_2F_5)_3PF_3$)

In a reaction vessel, 2.6 g of Intermediate-20, 10 mL of water and 2 mL of 35% hydrochloric acid were added, and cooled with salt-ice bath while stirring. The aqueous solution dissolved 0.7 g of sodium nitrite in 5 mL of water was added slowly at 0° C. while stirring, and stirred at 0° C. for one hour. The aqueous solution dissolved 5.3 g of K $(C_2F_5)_3PF_3$ in 50 mL of water was added there while maintaining the temperature, and stirred for 6 hours in addition. 50 mL of dichloromethane was added there, and the reaction mixture was extracted with 50 mL of dichloromethane. Then, the water layer was removed by liquid separation. The organic layer was washed with water five times, and concentrated by evaporator. By crystallization with diethylether, 2.9 g of pale yellow solid was obtained (Yield 41%). It was confirmed by $^1$H-, $^{19}$F-, $^{31}$P-NMR that this pale yellow solid product was axial ligand precursor (b-13/$(C_2F_5)_3PF_3$).

Production Example 29, Synthesis of Axial Ligand Precursor (b-13/Ga $(C_6F_5)$ 4)

3.7 g of pale yellow solid was obtained (Yield 37%) as in Production Example 28 (2), except that "5.3 g of K $(C_2F_5)$ $3PF_3$" was replaced with "8.4 g of $NaGa(C_6F_5)_4$ (dissolved in 100 mL of water)". It was confirmed by 1H-, $^{19}$F-NMR that this pale yellow solid product was axial ligand precursor (b-13/$Ga(C_6F_5)_4$).

Production Example 30, Synthesis of Axial Ligand Precursor (b-14/$(C_2F_5)_3PF_3$)

(1) Intermediate-21: Synthesis of 4-(hydroxyethoxyethoxy)ethyl-2,6-methoxyaniline 2.5 g of pale yellow oily product was obtained as in Production Example 28(1), except that "1.7 g of 2-(2-hydroxyethoxy)ethyl bromide" was replaced with "2.1 g of 2-(2-hydroxyethoxyethoxy)ethyl bromide". It was confirmed by 1H-NMR that this pale yellow oily product was Intermediate-21.

(2) Axial Ligand Precursor (b-14/$(C_2F_5)_3PF_3$)

3.7 g of pale yellow solid was obtained (Yield 40%) as in Production Example 28(2), except that "2.6 g of Intermediate-20" was replaced with "3.0 g of Intermediate-21". It was confirmed by 1H-, $^{19}$F-, $^{31}$P-NMR that this pale yellow solid product was axial ligand precursor (b-14/$(C_2F_5)_3PF_3$).

Production Example 31, Synthesis of Axial Ligand Precursor (b-15/C $(CF_3SO_2)$ 3)

(1) Intermediate-22: Synthesis of 2-methoxy-4-(isopropoxydimethylsilylpropyl)aniline In a reaction vessel, 1.6 g of 2-methoxy-4-allylaniline, 0.01 g of 1,3-divinyltetramethyldisiloxane-platinum complex (0.1M xylene solution) and 5 mL of toluene were added. Then 1.2 g of isopropoxydimethylsilane was added there, and allowed to react at 100° C. for 12 hours. After removing solvent, the residue was purified by silica gel column chromatography, so that 2.8 g of pale yellow oily product was obtained. It was confirmed by 1H-NMR that this pale yellow oily product was Intermediate-22.

(2) Axial Ligand Precursor (b-15/$C(CF_3SO_2)_3$)

2.9 g of pale yellow solid was obtained (yield 44%) as in Production Example 28(2), except that "2.6 g of Intermediate-20" was replaced with "2.8 g of Intermediate-22" and "5.3 g of $K(C_2F_5)_3PF_3$" was replaced with "4.9 g of $KC(CF_3SO_2)_3$". It was confirmed by 1H-, $^{19}$F-NMR that this pale yellow solid product was axial ligand precursor (b-15/$C(CF_3SO_2)_3$).

<Examples 1 to 53> (Synthesis of Photoacid Generators of the Present Invention)

Photoacid generators of the present invention were synthesized based on the following synthesis methods (I to III). The structure and synthesis method of photoacid generator (abbreviated as PAG) synthesized in Examples 1 to 53 are shown in Table 1.

Synthesis Method (I) (in Case of Metal Complex Having 2 Axial Ligands)

Examples 1 to 21, 32 to 41, 46 to 53

In a reaction vessel, a metal complex precursor (a) and an axial ligand precursor ($b/X_1$-), mole ratio 1:2, were mixed in acetonitrile solvent at room temperature, and allowed to react for 6 hours while blowing nitrogen gas. An aimed product (photoacid generator) was obtained by removing acetonitrile under reduced pressure.

Synthesis Method (II) (in Case of Cationic Metal Complex Having 2 Axial Ligands and Having Counter Anion $X_2^-$)

Examples 30, 31, 42 to 45

In a reaction vessel, a metal complex precursor (a) and an axial ligand precursor ($b/X_1^-$), mole ratio 1:2, were mixed in acetonitrile solvent at room temperature, and allowed to react for 6 hours while blowing nitrogen gas. After removing acetonitrile under reduced pressure, the residue was dissolved in dichloromethane. An aqueous solution of alkali metal salt (lithium, sodium or potassium salt) of anion $X_2^-$ was added there, and stirred for one hour. The reaction mixture was allowed to stand still, and the water layer was removed by liquid separation. The organic layer was washed with water five times, and concentrated. The concentrate was purified by dichloromethane-hexane, so that an aimed product (photoacid generator) was obtained.

Synthesis Method (III) (in Case of Metal Complex Having One Axial Ligand)

Examples 22 to 29

In a reaction vessel, a metal complex precursor (a) and an axial ligand precursor ($b-2/X_1^-$) synthesized in Production Example 12, mole ratio 1:1, were mixed in acetonitrile solvent at room temperature, and allowed to react for 6 hours while blowing nitrogen gas. An aimed product (photoacid generator) was obtained by removing acetonitrile under reduced pressure.

TABLE 1

| | | CL | CM | ALS(Cation) | | Anion Structure | | | MCP | ALP |
|---|---|---|---|---|---|---|---|---|---|---|
| Example | | (CH) | (M) | $L^1$ | $L^2$ | $X_1$ | $X_2$ | SM | (a) | (b) |
| 1 | PAG-1 | CH-1 | Si | LS-1 | LS-1 | $PF_6$ | — | I | a-1 | b-1 |
| 2 | PAG-2 | CH-1 | Si | LS-1 | LS-1 | $SbF_6$ | — | I | a-1 | b-1 |
| 3 | PAG-3 | CH-1 | Si | LS-1 | LS-1 | $B(C_6F_5)_4$ | — | I | a-1 | b-1 |
| 4 | PAG-4 | CH-1 | Si | LS-1 | LS-1 | $(C_2F_5)_3PF_3$ | — | I | a-1 | b-1 |
| 5 | PAG-5 | CH-1 | Si | LS-1 | LS-1 | $Ga(C_6F_5)_4$ | — | I | a-1 | b-1 |
| 6 | PAG-6 | CH-1 | Si | LS-1 | LS-1 | $Al(O^{t-}C4H$ | — | I | a-1 | b-1 |
| 7 | PAG-7 | CH-1 | Si | LS-1 | LS-1 | $(CF_3SO_2)_3C$ | — | I | a-1 | b-1 |
| 8 | PAG-8 | CH-1 | Si | LS-4 | LS-4 | $PF_6$ | — | I | a-1 | b-2 |
| 9 | PAG-9 | CH-1 | Si | LS-4 | LS-4 | $(C_2F_5)_3PF_3$ | — | I | a-1 | b-2 |
| 1 | PAG-1 | CH-1 | Si | LS-5 | LS-5 | $Ga(C_6F_5)_4$ | — | I | a-1 | b-3 |
| 1 | PAG-1 | CH-1 | Si | LS-7 | LS-7 | $B(C_6F_5)_4$ | — | I | a-1 | b-4 |
| 1 | PAG-1 | CH-1 | Si | LS-8 | LS-8 | $Ga(C_6F_5)_4$ | — | I | a-1 | b-5 |
| 1 | PAG-1 | CH-1 | Si | LS-1 | LS-1 | $(C_2F_5)_3PF_3$ | — | I | a-1 | b-6 |
| 1 | PAG-1 | CH-1 | Si | LS-1 | LS-1 | $Ga(C_6F_5)_4$ | — | I | a-1 | b-7 |
| 1 | PAG-1 | CH-1 | Si | LS-1 | LS-1 | $(C_2F_5)_3PF_3$ | — | I | a-1 | b-8 |
| 1 | PAG-1 | CH-1 | Si | LI-1 | LI-1 | $Al(O^{t-}C4H$ | — | I | a-1 | b-9 |
| 1 | PAG-1 | CH-1 | Si | LI-2 | LI-2 | $Al(O^{t-}C4H$ | — | I | a-1 | b-10 |
| 1 | PAG-1 | CH-1 | Si | LI-5 | LI-5 | $(C_2F_5)_3PF_3$ | — | I | a-1 | b-12 |
| 1 | PAG-1 | CH-1 | Si | LN-1 | LN-1 | $(C_2F_5)_3PF_3$ | — | I | a-1 | b-13 |
| 2 | PAG-2 | CH-1 | Si | LN-2 | LN-2 | $(C_2F_5)_3PF_3$ | — | I | a-1 | b-14 |
| 2 | PAG-2 | CH-1 | Si | LN-4 | LN-4 | $(CF_3SO_2)_3C$ | — | I | a-1 | b-15 |
| 2 | PAG-2 | CH-2 | P | LS-1 | LS-1 | $PF_6$ | $PF_6$ | II | a-2 | b-1 |
| 2 | PAG-2 | CH-2 | P | LS-1 | LS-1 | $B(C_6F_5)_4$ | $B(C_6F_5)_4$ | II | a-2 | b-1 |
| 2 | PAG-2 | CH-2 | P | LS-1 | LS-1 | $(C_2F_5)_3PF_3$ | $(C_2F_5)_3PF_3$ | II | a-2 | b-1 |

TABLE 1-continued

| | CL | CM | ALS(Cation) | | Anion Structure | | | MCP | ALP |
|---|---|---|---|---|---|---|---|---|---|
| Example | (CH) | (M) | $L^1$ | $L^2$ | $X_1$ | $X_2$ | SM | (a) | (b) |
| 2 PAG-2 | CH-2 | P | LS-1 | LS-1 | $Ga(C_6F_5)_4$ | $Ga(C_6F_5)_4$ | II | a-2 | b-1 |
| 2 PAG-2 | CH-2 | P | LS-1 | LS-1 | $Al(O^t$-C4H | $Al(O^t$-C4H | II | a-2 | b-1 |
| 2 PAG-2 | CH-2 | P | LI-4 | LI-4 | $(C_2F_5)_3PF_3$ | $(C_2F_5)_3PF_3$ | II | a-2 | b-11 |
| 2 PAG-2 | CH-2 | P | LN-1 | LN-1 | $Ga(C_6F_5)_4$ | $Ga(C_6F_5)_4$ | II | a-2 | b-13 |
| 2 PAG-2 | CH-2 | Sb | LS-4 | LS-4 | $SbF_6$ | $SbF_6$ | II | a-3 | b-2 |
| 3 PAG-3 | CH-2 | Fe | LS-4 | — | $PF_6$ | — | III | a-4 | b-2 |
| 3 PAG-3 | CH-2 | Mn | LS-4 | — | $PF_6$ | — | III | a-5 | b-2 |
| 3 PAG-3 | CH-3 | Si | LS-1 | LS-1 | $PF_6$ | — | I | a-6 | b-1 |
| 3 PAG-3 | CH-4 | Si | LS-1 | LS-1 | $PF_6$ | — | I | a-7 | b-1 |
| 3 PAG-3 | CH-4 | Si | LS-1 | LS-1 | $SbF_6$ | — | I | a-7 | b-1 |
| 3 PAG-3 | CH-4 | Si | LS-1 | LS-1 | $B(C_6F_5)_4$ | — | I | a-7 | b-1 |
| 3 PAG-3 | CH-4 | Si | LS-1 | LS-1 | $(C_2F_5)_3PF_3$ | — | I | a-7 | b-1 |
| 3 PAG-3 | CH-4 | Si | LS-1 | LS-1 | $Ga(C_6F_5)_4$ | — | I | a-7 | b-1 |
| 3 PAG-3 | CH-4 | Si | LS-1 | LS-1 | $Al(O^t$-C4H | — | I | a-7 | b-1 |
| 3 PAG-3 | CH-4 | Si | LS-1 | LS-1 | $(CF_3SO_2)_3C$ | — | I | a-7 | b-1 |
| 4 PAG-4 | CH-4 | Ge | LS-1 | LS-1 | $PF_6$ | — | I | a-8 | b-1 |
| 4 PAG-4 | CH-4 | Ge | LI-1 | LI-1 | $(C_2F_5)_3PF_3$ | — | I | a-8 | b-9 |
| 4 PAG-4 | CH-4 | Ga | LS-1 | — | $Ga(C_6F_5)_4$ | — | III | a-9 | b-1 |
| 4 PAG-4 | CH-4 | Ga | LI-1 | — | $Ga(C_6F_5)_4$ | — | III | a-9 | b-9 |
| 4 PAG-4 | CH-4 | In | LS-1 | — | $B(C_6F_5)_4$ | — | III | a-10 | b-1 |
| 4 PAG-4 | CH-4 | In | LI-1 | — | $B(C_6F_5)_4$ | — | III | a-10 | b-9 |
| 4 PAG-4 | CH-5 | Al | LS-1 | — | $Al(O^t$-C4H | — | III | a-11 | b-1 |
| 4 PAG-4 | CH-5 | Al | LI-1 | — | $Al(O^t$-C4H | — | III | a-11 | b-9 |
| 4 PAG-4 | CH-6 | Si | LS-1 | LS-1 | $PF_6$ | — | I | a-12 | b-1 |
| 4 PAG-4 | CH-7 | Ti | LS-1 | LS-1 | $PF_6$ | — | I | a-13 | b-1 |
| 5 PAG-5 | CH-8 | Si | LS-1 | LS-1 | $(C_2F_5)_3PF_3$ | — | I | a-14 | b-1 |
| 5 PAG-5 | CH-8 | Si | LI-1 | LI-1 | $(C_2F_5)_3PF_3$ | — | I | a-14 | b-9 |
| 5 PAG-5 | CH-8 | Sn | LS-1 | LS-1 | $B(C_6F_5)_4$ | — | I | a-15 | b-1 |
| 5 PAG-5 | CH-8 | Sn | LI-1 | LI-1 | $B(C_6F_5)_4$ | — | I | a-15 | b-9 |

CL represents cyclic ligand.
CM represents central metal.
ALS represents axial ligand structure.
SM represents synthesis method.
MCP represents metal complex precursor.
ALP represents axial ligand precursor.

Evaluation

<Examples 54 to 126 and Comparative Examples 1 to 14>[Preparation of Photosensitive Composition-1]

100 g of the cationically polymerizable compound (C) and the photoacid generator of the present invention, (PAG-1 to PAG-53), were mixed uniformly, so that photosensitive compositions, (Q-1) to (Q-146), were prepared. Also, 100 g of the cationically polymerizable compound (C) and the comparative photoacid generator, (H-1 to H-3), and the sensitizer (B) were mixed uniformly, so that comparative photosensitive compositions, (Q'-1) to (Q'-14), were prepared. The type and amount of raw materials used are shown in Table 2 to Table 7.

Raw Materials Used

PAG-1 to PAG-53 (photoacid generator described in Table 1)
H-1: CPI-210S (manufactured by San-Apro Ltd.)
H-2: di(tert-butylphenyl)iodonium hexafluorophosphate (manufactured by Tokyo Chemical Industry Co., Ltd.)
H-3: 4-isopropyl-4'-methyldiphenyliodonium tetrakis (pentafluorophenyl)borate (manufactured by Tokyo Chemical Industry Co., Ltd.)
B-1: tetraphenylporphyrin (manufactured by Tokyo Chemical Industry Co., Ltd.)
B-2: phthalocyanine (manufactured by Tokyo Chemical Industry Co., Ltd.)
C-1: Product Name, CELLOXIDE 2021P (manufactured by Daicel Chemical Industries, Ltd.)
C-2: Product Name, jER828 (manufactured by Mitsubishi Chemical Group Corporation)
C-3: Product Name, OXT-221 (manufactured by Toagosei Company, Limited)
C-4: Product Name, ETERNACOLL OXBP (manufactured by UBE Corporation; registered Trademark)
C-5: Product Name, THI-DE (manufactured by ENEOS Corporation)

[Curability]

Curing Test: The photosensitive composition of the present invention or the comparative photosensitive composition was applied to a glass substrate (76 mm×52 mm) using an applicator (40 μm), and exposed to light using an irradiator LIGHTNINGCURE Spot:Light Source LC 8 (manufactured by Hamamatsu Photonics K.K.) as a light source under the following conditions, and curing test was examined.

Curability-1: Infrared transmission filter $R_{64}$ (cutting light having a wavelength of 620 nm or less) (manufactured by HOYA CORPORATION)
Curability-2: Infrared transmission filter $R_{72}$ (cutting light having a wavelength of 700 nm or less) (manufactured by HOYA CORPORATION)

Then, curability was examined by the following evaluation method. The results are shown in Table 2 to 7.

Evaluation of Curability:

⊚ The surface has no tackiness, and is not scratched even when scraped with a nail.
○ The surface has no tackiness, but is scratched with a nail.
Δ The surface remains tacky.
× The composition remains liquid, and is not cured.

TABLE 2

| | | | | Cationically polymerizable compound (C) | | | | | Curability |
|---|---|---|---|---|---|---|---|---|---|
| EX | PSC | PAG | Amount | C-1 | C-2 | C-3 | C-4 | C-5 | Curability-1 |
| 54 | Q-1 | PAG-1 | 3.0 | 100 | — | — | — | — | ◎ |
| 55 | Q-2 | PAG-2 | 1.0 | 100 | — | — | — | — | ◎ |
| 56 | Q-3 | PAG-3 | 1.0 | 100 | — | — | — | — | ◎ |
| 57 | Q-4 | PAG-4 | 1.0 | 100 | — | — | — | — | ◎ |
| 58 | Q-5 | PAG-5 | 1.0 | 100 | — | — | — | — | ◎ |
| 59 | Q-6 | PAG-6 | 1.0 | 100 | — | — | — | — | ◎ |
| 60 | Q-7 | PAG-7 | 1.0 | 100 | — | — | — | — | ◎ |
| 61 | Q-8 | PAG-8 | 3.0 | 100 | — | — | — | — | ◎ |
| 62 | Q-9 | PAG-9 | 1.0 | 100 | — | — | — | — | ◎ |
| 63 | Q-10 | PAG-10 | 1.0 | 100 | — | — | — | — | ◎ |
| 64 | Q-11 | PAG-11 | 1.0 | 100 | — | — | — | — | ◎ |
| 65 | Q-12 | PAG-12 | 1.0 | 100 | — | — | — | — | ◎ |
| 66 | Q-13 | PAG-13 | 1.0 | 100 | — | — | — | — | ◎ |
| 67 | Q-14 | PAG-14 | 1.0 | 100 | — | — | — | — | ◎ |
| 68 | Q-15 | PAG-15 | 1.0 | 100 | — | — | — | — | ◎ |
| 69 | Q-16 | PAG-16 | 1.0 | 100 | — | — | — | — | ◎ |
| 70 | Q-17 | PAG-17 | 1.0 | 100 | — | — | — | — | ◎ |
| 71 | Q-18 | PAG-18 | 1.0 | 100 | — | — | — | — | ◎ |
| 72 | Q-19 | PAG-19 | 1.0 | 100 | — | — | — | — | ◎ |
| 73 | Q-20 | PAG-20 | 1.0 | 100 | — | — | — | — | ◎ |
| 74 | Q-21 | PAG-21 | 1.0 | 100 | — | — | — | — | ◎ |
| 75 | Q-22 | PAG-22 | 3.0 | 100 | — | — | — | — | ◎ |
| 76 | Q-23 | PAG-23 | 1.0 | 100 | — | — | — | — | ◎ |
| 77 | Q-24 | PAG-24 | 1.0 | 100 | — | — | — | — | ◎ |
| 78 | Q-25 | PAG-25 | 1.0 | 100 | — | — | — | — | ◎ |
| 79 | Q-26 | PAG-26 | 1.0 | 100 | — | — | — | — | ◎ |
| 80 | Q-27 | PAG-27 | 1.0 | 100 | — | — | — | — | ◎ |
| 81 | Q-28 | PAG-28 | 1.0 | 100 | — | — | — | — | ◎ |
| 82 | Q-29 | PAG-29 | 1.0 | 100 | — | — | — | — | ◎ |
| 83 | Q-30 | PAG-30 | 3.0 | 100 | — | — | — | — | ◎ |
| 84 | Q-31 | PAG-31 | 3.0 | 100 | — | — | — | — | ◎ |
| 85 | Q-32 | PAG-32 | 3.0 | 100 | — | — | — | — | ◎ |

EX represents Example.
PSC represents Photosensitive Composition.
PAG represents Photoacid Generator.

TABLE 3

| | | | | Cationically polymerizable compound (C) | | | | | Curability |
|---|---|---|---|---|---|---|---|---|---|
| EX | PSC | PAG | Amount | C-1 | C-2 | C-3 | C-4 | C-5 | Curability-1 |
| 86 | Q-54 | PAG-4 | 1.0 | — | 100 | — | — | — | ◎ |
| 87 | Q-55 | PAG-4 | 1.0 | 30 | — | 70 | — | — | ◎ |
| 88 | Q-56 | PAG-4 | 1.0 | 30 | — | — | 70 | — | ◎ |
| 89 | Q-57 | PAG-4 | 1.0 | 80 | — | — | — | 20 | ◎ |
| 90 | Q-58 | PAG-4 | 1.0 | 50 | 50 | — | — | — | ◎ |
| 91 | Q-59 | PAG-4 | 1.0 | — | — | 80 | — | 20 | ◎ |
| 92 | Q-60 | PAG-4 | 1.0 | — | — | — | 80 | 20 | ◎ |
| 93 | Q-61 | PAG-4 | 1.0 | — | 80 | — | — | 20 | ◎ |
| 94 | Q-62 | PAG-4 | 1.0 | 60 | — | — | 40 | — | ◎ |
| 95 | Q-63 | PAG-4 | 1.0 | 70 | — | 30 | — | — | ◎ |
| 96 | Q-64 | PAG-4 | 1.0 | — | 40 | 60 | — | — | ◎ |
| 97 | Q-65 | PAG-4 | 1.0 | — | 30 | — | 50 | 20 | ◎ |
| 98 | Q-66 | PAG-16 | 1.0 | — | 100 | — | — | — | ◎ |
| 99 | Q-67 | PAG-16 | 1.0 | 30 | — | 70 | — | — | ◎ |
| 100 | Q-68 | PAG-16 | 1.0 | 30 | — | — | 70 | — | ◎ |
| 101 | Q-69 | PAG-16 | 1.0 | 80 | — | — | — | 20 | ◎ |
| 102 | Q-70 | PAG-25 | 1.0 | — | 100 | — | — | — | ◎ |
| 103 | Q-71 | PAG-25 | 1.0 | 30 | — | 70 | — | — | ◎ |
| 104 | Q-72 | PAG-25 | 1.0 | 30 | — | — | 70 | — | ◎ |
| 105 | Q-73 | PAG-25 | 1.0 | 80 | — | — | — | 20 | ◎ |

EX, PSC and PAG are the same as in Table 2.

TABLE 4

| | | | | Cationically polymerizable compound (C) | | | | | Curability |
|---|---|---|---|---|---|---|---|---|---|
| EX | PSC | PAG | Amount | C-1 | C-2 | C-3 | C-4 | C-5 | Curability-2 |
| 106 | Q-33 | PAG-33 | 3.0 | 100 | — | — | — | — | ⊚ |
| 107 | Q-34 | PAG-34 | 1.0 | 100 | — | — | — | — | ⊚ |
| 108 | Q-35 | PAG-35 | 3.0 | 100 | — | — | — | — | ⊚ |
| 109 | Q-36 | PAG-36 | 3.0 | 100 | — | — | — | — | ⊚ |
| 110 | Q-37 | PAG-37 | 3.0 | 100 | — | — | — | — | ⊚ |
| 111 | Q-38 | PAG-38 | 3.0 | 100 | — | — | — | — | ⊚ |
| 112 | Q-39 | PAG-39 | 3.0 | 100 | — | — | — | — | ⊚ |
| 113 | Q-40 | PAG-40 | 1.0 | 100 | — | — | — | — | ⊚ |
| 114 | Q-41 | PAG-41 | 1.0 | 100 | — | — | — | — | ⊚ |
| 115 | Q-42 | PAG-42 | 1.0 | 100 | — | — | — | — | ⊚ |
| 116 | Q-43 | PAG-43 | 1.0 | 100 | — | — | — | — | ⊚ |
| 117 | Q-44 | PAG-44 | 1.0 | 100 | — | — | — | — | ⊚ |
| 118 | Q-45 | PAG-45 | 1.0 | 100 | — | — | — | — | ⊚ |
| 119 | Q-46 | PAG-46 | 1.0 | 100 | — | — | — | — | ⊚ |
| 120 | Q-47 | PAG-47 | 1.0 | 100 | — | — | — | — | ⊚ |
| 121 | Q-48 | PAG-48 | 3.0 | 100 | — | — | — | — | ⊚ |
| 122 | Q-49 | PAG-49 | 3.0 | 100 | — | — | — | — | ⊚ |
| 123 | Q-50 | PAG-50 | 1.0 | 100 | — | — | — | — | ⊚ |
| 124 | Q-51 | PAG-51 | 1.0 | 100 | — | — | — | — | ⊚ |
| 125 | Q-52 | PAG-52 | 1.0 | 100 | — | — | — | — | ⊚ |
| 126 | Q-53 | PAG-53 | 1.0 | 100 | — | — | — | — | ⊚ |

EX, PSC and PAG are the same as in Table 2.

TABLE 5

| | | | | Cationically polymerizable compound (C) | | | | | Curability |
|---|---|---|---|---|---|---|---|---|---|
| EX | PSC | PAG | Amount | C-1 | C-2 | C-3 | C-4 | C-5 | Curability-2 |
| 127 | Q-74 | PAG-36 | 1.0 | | 100 | — | — | — | ⊚ |
| 128 | Q-75 | PAG-36 | 1.0 | 30 | — | 70 | — | — | ⊚ |
| 129 | Q-76 | PAG-36 | 1.0 | 30 | — | — | 70 | — | ⊚ |
| 130 | Q-77 | PAG-36 | 1.0 | 80 | — | — | — | 20 | ⊚ |
| 131 | Q-78 | PAG-36 | 1.0 | 50 | 50 | — | — | — | ⊚ |
| 132 | Q-79 | PAG-36 | 1.0 | — | — | 80 | — | 20 | ⊚ |
| 133 | Q-80 | PAG-36 | 1.0 | — | — | — | 80 | 20 | ⊚ |
| 134 | Q-81 | PAG-36 | 1.0 | — | 80 | — | — | 20 | ⊚ |
| 135 | Q-82 | PAG-36 | 1.0 | 60 | — | — | 40 | — | ⊚ |
| 136 | Q-83 | PAG-36 | 1.0 | 70 | — | 30 | — | — | ⊚ |
| 137 | Q-84 | PAG-36 | 1.0 | — | 40 | 60 | — | — | ⊚ |
| 138 | Q-85 | PAG-36 | 1.0 | — | 30 | — | 50 | 20 | ⊚ |
| 139 | Q-86 | PAG-43 | 1.0 | — | 100 | — | — | — | ⊚ |
| 140 | Q-87 | PAG-43 | 1.0 | 30 | — | 70 | — | — | ⊚ |
| 141 | Q-88 | PAG-43 | 1.0 | 30 | — | — | 70 | — | ⊚ |
| 142 | Q-89 | PAG-43 | 1.0 | 80 | — | — | — | 20 | ⊚ |
| 143 | Q-90 | PAG-47 | 1.0 | — | 100 | — | — | — | ⊚ |
| 144 | Q-91 | PAG-47 | 1.0 | 30 | — | 70 | — | — | ⊚ |
| 145 | Q-92 | PAG-47 | 1.0 | 30 | — | — | 70 | — | ⊚ |
| 146 | Q-93 | PAG-47 | 1.0 | 80 | — | — | — | 20 | ⊚ |

EX, PSC and PAG are the same as in Table 2.

TABLE 6

| CEX | PSC | PAG | Amount | Sensitizer (B) | Amount | CPC (C) C-1 | Curability Curability-1 |
|---|---|---|---|---|---|---|---|
| 1 | Q'-1 | H-1 | 2.0 | B-1 | 0.5 | 100 | X |
| 2 | Q'-2 | H-2 | 2.0 | B-1 | 0.5 | 100 | X |
| 3 | Q'-3 | H-3 | 2.0 | B-1 | 0.5 | 100 | Δ |
| 4 | Q'-4 | H-3 | 5.0 | B-1 | 0.5 | 100 | Δ |
| 5 | Q'-5 | H-3 | 2.0 | B-2 | 0.5 | 100 | X |
| 6 | Q'-6 | H-3 | 2.0 | B-1 | 1.0 | 100 | Δ |
| 7 | Q'-7 | H-3 | 2.0 | B-1 | 2.0 | 100 | Δ |

PSC and PAG are the same as in Table 2.

CEX represents Comparative Example.

CPC represents Cationically polymerizable compound.

TABLE 7

| CEX | PSC | PAG | Amount | Sensitizer (B) | Amount | CPC (C) C-1 | Curability Curability-2 |
|---|---|---|---|---|---|---|---|
| 8 | Q'-8 | H-1 | 2.0 | B-2 | 0.5 | 100 | X |
| 9 | Q'-9 | H-2 | 2.0 | B-2 | 0.5 | 100 | X |
| 10 | Q'-10 | H-3 | 1.0 | B-2 | 0.5 | 100 | X |
| 11 | Q'-11 | H-3 | 2.0 | B-2 | 0.5 | 100 | Δ |
| 12 | Q'-12 | H-3 | 5.0 | B-2 | 0.5 | 100 | Δ |
| 13 | Q'-13 | H-3 | 2.0 | B-2 | 1.0 | 100 | Δ |
| 14 | Q'-14 | H-3 | 2.0 | B-2 | 2.0 | 100 | Δ |

CEX, PSC, PAG and CPC are the same as in Table 6.

From the results of Examples 54 to 146 and Comparative Examples 1 to 14 in Table 2 to Table 7, it is found that the photosensitive compositions comprising the photoacid generators of the present invention have an excellent curability, when performing exposure to light in a visible to infrared region, compared with the comparative photosensitive compositions. The photoacid generator of the present invention has an onium salt structure as the axial ligand which is an acid generating site. The onium salt structure as the axial ligand is adjacent to aromatic heterocyclic compound which is a cyclic ligand and also a site of absorption, therefore the onium salt generates acid very efficiently. The Comparative Examples are the cases that cyclic compound having the same structure as a sensitizer was added separately, but the curability is inferior, compared with Examples of the present invention, therefore the acid generating efficiency is poor. From the results of Examples 86 to 105 and Examples 127 to 146, it is found that the photosensitive compositions have the same curability regardless of type of cationically polymerizable compounds.

Examples 147 to 158: Examples of Photosensitive Composition Containing Additives (J)

[Preparation of Photosensitive Composition-2]

30 g of titanium oxide (Ja-1, TIPAQUE R-930 manufactured by ISHIHARA SANGYO KAISHA, LTD.) or 30 g of Direct Blue (Ja-2, manufactured by Tokyo Chemical Industry Co., Ltd.) as an additive, 3 g of pigment dispersant (SOLSPERSE 32000 manufactured by Lubrizol Corporation), 60 g of cationically polymerizable compound (C-1) and 1 g of photoacid generator of the present invention were added, and kneaded at 25° C. for 3 hours by using ball mill, so that photosensitive compositions of the present invention, (Q-94) to (Q-105), were produced. The coating film curability (curability-3 and -4) was evaluated by the following method. The results are shown in Table 8.

[Curability]

Curability-3 and -4: The above photosensitive compositions were applied using a bar coater to a surface treated PET (polyethylene terephthalate) film with a thickness 100 μm [Cosmo Shine A4300 manufactured by TOYOBO CO., LTD.] to be coating film thickness 20 μm (Curability-3) and coating film thickness 100 μm (Curability-4). These coating films were exposed to light using an irradiator LIGHTNINGCURE Spot Light Source LC 8 (manufactured by Hamamatsu Photonics K.K.) as a light source. Then, curability was examined by the following evaluation method.

Evaluation of Curability:

◎ The surface has no tackiness, and is not scratched even when scraped with a nail.

○ The surface has no tackiness, but is scratched with a nail.

Δ The surface remains tacky.

× The composition remains liquid, and is not cured.

TABLE 8

| EX | PSC | PAG | Additive (J) | Curability: Curability-3 | Curability: Curability-4 |
|---|---|---|---|---|---|
| 147 | Q-94 | PAG-4 | Ja-1 | ◎ | ◎ |
| 148 | Q-95 | PAG-16 | Ja-1 | ◎ | ◎ |
| 149 | Q-96 | PAG-25 | Ja-1 | ◎ | ◎ |
| 150 | Q-97 | PAG-36 | Ja-1 | ◎ | ◎ |
| 151 | Q-98 | PAG-43 | Ja-1 | ◎ | ◎ |
| 152 | Q-99 | PAG-47 | Ja-1 | ◎ | ◎ |
| 153 | Q-100 | PAG-4 | Ja-2 | ◎ | ◎ |
| 154 | Q-101 | PAG-16 | Ja-2 | ◎ | ◎ |
| 155 | Q-102 | PAG-25 | Ja-2 | ◎ | ◎ |
| 156 | Q-103 | PAG-36 | Ja-2 | ◎ | ◎ |
| 157 | Q-104 | PAG-43 | Ja-2 | ◎ | ◎ |
| 158 | Q-105 | PAG-47 | Ja-2 | ◎ | ◎ |

EX, PSC and PAG are the same as in Table 2.

From the results in Table 8, it is found that the photosensitive compositions of the present invention are possible to cure efficiently, even when a substance such as a colorant which attenuates or blocks irradiated light is present at a high concentration. Also, as a comparison, H-3 as a photoacid generator and B-2 as a sensitizer were used instead of the photoacid generator of the present invention, but, a cured product was not obtained.

INDUSTRIAL APPLICABILITY

The photosensitive composition of the present invention utilizes light (particularly in a visible to infrared region), and is suitably used for paints, coating agents, various coating materials (hard coats, anti-fouling coating materials, anti-fogging coating materials, anti-corrosion coating materials, optical fibers and the like), back surface treatment agents for pressure sensitive adhesive tapes, release coating materials of release sheets for pressure sensitive adhesive labels (release papers, release plastic films, release metal foils and the like), printing plates, dental materials (dental formulations and dental composites), ink compositions, inkjet ink compositions, positive resists (for formation of connection terminals and wiring patterns in production of electronic components such as circuit boards, CSP and MEMS elements), resist films, liquid resists and negative resists (permanent film materials of surface protecting films, interlayer dielectric films, planarizing films for semiconductor elements and transparent electrodes for FPD (ITO, IZO and GZO), and the like), resists for MEMS, positive photosensitive materials, negative photosensitive materials, various adhesives (various temporary fixing agents for electronic components, adhesives for HDD, adhesives for pick-up lenses, functional films for FPD (polarizing plates, antireflection films and the like), insulating films for circuit formation and semiconductor sealing, anisotropic electroconductive adhesives (ACA), films (ACF), pastes (ACP) and the like), holographic resins, FPD materials (color filters, black matrices, partition wall materials, photospacers, ribs, orientation films for liquid crystals, sealing agents for FPD and the like), optical members, molding materials (for building materials, optical components and lenses), casting materials, putty materials, glass fiber impregnating agents, fillers, sealing materials, flip-chips, chip sealants for COF and the like, sealants for packages such as CSP or BGA, photosemiconductor (LED) sealing materials, optical waveguide materials, nano-imprint materials, stereolithography materials, micro-stereolithography materials and the like.

The invention claimed is:

1. A photoacid generator that is a metal complex having, as a ligand, a ring structure formed by bonding five-membered ring aromatic heterocyclic compounds directly or by π-conjugation, wherein a central metal has one or two axial ligands, and the axial ligand has an onium salt structure, wherein the metal complex is represented by general Formula (1) or general Formula (2):

[Formula 1]

(1)

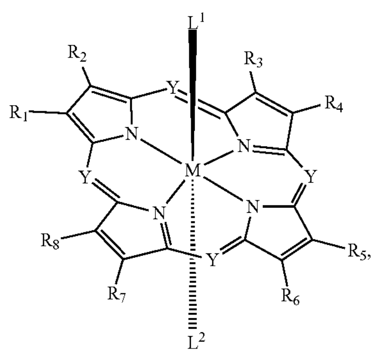

in Formula (1), $R_1$ to $R_5$ are a substituent of the aromatic heterocycle, $R_1$ and $R_2$, $R_3$ and $R_4$, $R_5$ and $R_6$, $R_7$ and $R_8$ may be bonded each other to form a condensed polycyclic aromatic structure;

Y represents a nitrogen atom, a carbon atom or may be bonded directly, when Y represents a carbon atom, the carbon atom is substituted with a hydrogen atom or an aromatic hydrocarbon having 6 to 14 carbon atoms: M is selected from the group consisting of Al, Ga, In, Si, Ge, Sn, Fe, Ti, Co and Mn; $L^1$ and $L^2$ are an axial ligand coordinated to the central metal, represented by Formula (3), when M is Al, G&, In, Fe, Co or Mn, the central metal has $L^1$ only as the axial ligand:

[Formula 2]

(2)

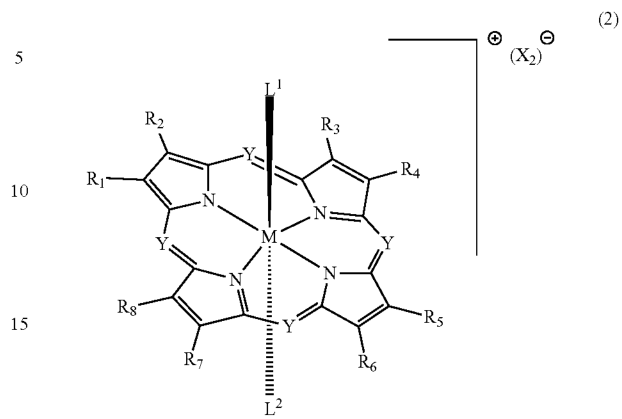

in Formula (2) represents a case when the central metal M is cationic: $R_1$ to $R_8$, Y, $L^1$ and $L^2$ are the same as these of Formula (1); M is selected from the grout consisting of P, Sb and Bi; $X_2^-$ represents a monovalent counter anion corresponding to the central metal cation,

[Formula 3]

(3)

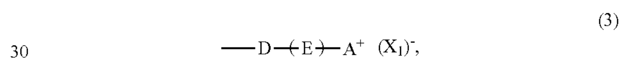

in Formula (3), D represents an oxygen atom or a sulfur atom: E represents an alkylene group having 1 to 8 carbon atoms, an alkenylene group having 2 to 8 carbon atoms, an alkynilene group having 2 to 8 carbon atoms or an arylene group having 6 to 14 carbon atoms, a main chain of E may contain an ether group, a sulfide group, a ketone group, an amide group, an ester group, a thioester group, an urea group, a sulfone group, a silyl group or a phenylene group: $A^+$ represents a monovalent onium cation selected from a sulfonium cation, a diazonium cation or an iodonium cation: $X_1^-$ represents a monovalent counter anion corresponding to the onium cation.

2. The photoacid generator according to claim 1, wherein the ligand forming a ring structure is porphyrin or phthalocyanine.

3. A photosensitive composition, comprising the photoacid generator according to claim 1 and a cationically polymerizable compound.

4. A cured product obtained by curing the photosensitive composition according to claim 3.

* * * * *